US006828446B2

(12) United States Patent
Chandrakumar et al.

(10) Patent No.: US 6,828,446 B2
(45) Date of Patent: Dec. 7, 2004

(54) AROMATIC THIOETHER LIVER X-RECEPTOR MODULATORS

(75) Inventors: Nizal S. Chandrakumar, Vernon Hills, IL (US); Christopher R. Dalton, Mundelein, IL (US); James W. Malecha, Libertyville, IL (US); Michael B. Tollefson, Hainesville, IL (US); Jennifer Ann Van Camp, Glencoe, IL (US); Phillip B. Cox, Grayslake, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/327,741

(22) Filed: Dec. 23, 2002

(65) Prior Publication Data

US 2003/0207898 A1 Nov. 6, 2003

Related U.S. Application Data

(60) Provisional application No. 60/345,163, filed on Dec. 21, 2001.

(51) Int. Cl.$^7$ ...................... C07D 319/04; C07D 317/06
(52) U.S. Cl. ...................................... 549/362; 549/434
(58) Field of Search ................................ 549/434, 362; 514/469

(56) References Cited

U.S. PATENT DOCUMENTS

| | | | |
|---|---|---|---|
| 3,378,586 A | * | 4/1968 | Krapcho ..................... 564/182 |
| 3,755,605 A | | 8/1973 | Moore |
| 5,011,851 A | | 4/1991 | Meanwell |
| 5,639,616 A | | 6/1997 | Liao et al. |
| 5,690,904 A | | 11/1997 | MacWhorter et al. |
| 6,316,503 B1 | | 11/2001 | Li et al. |
| RE37,770 E | | 6/2002 | Elias et al. |
| 2001/0020030 A1 | | 9/2001 | Stewart et al. |
| 2002/0013334 A1 | | 1/2002 | Robl et al. |
| 2002/0048572 A1 | | 4/2002 | Shan et al. |
| 2002/0165394 A1 | | 11/2002 | Dumas et al. |

FOREIGN PATENT DOCUMENTS

| | | |
|---|---|---|
| EP | 0 135 894 A2 | 4/1985 |
| EP | 0453658 A2 | 10/1991 |
| EP | 0 558 062 A2 | 9/1993 |
| WO | WO 91/00277 | 1/1991 |
| WO | WO 91/00281 | 1/1991 |
| WO | WO 96/19493 | 6/1996 |
| WO | WO 96/34851 | 11/1996 |
| WO | WO 2000044715 | * 8/2000 |
| WO | WO 00/54759 | 9/2000 |
| WO | WO 00/55118 | 9/2000 |
| WO | WO 00/56710 | 9/2000 |
| WO | WO 01/60818 A1 | 8/2001 |
| WO | WO 02/20463 A2 | 3/2002 |
| WO | WO 02/24632 A2 | 3/2002 |
| WO | WO 02/46141 A2 | 6/2002 |
| WO | WO 02/46172 A2 | 6/2002 |
| WO | WO 02/46181 A2 | 6/2002 |

OTHER PUBLICATIONS

Yale et al, Journal of Medicinal Chemistry, vol. 13, No. 4, pp. 713–722, Dec. 1969.*
Ames et al, Journal of Chemical Society, Perkin Transactions 1, vol. 6, pp. 539–543, 1978.*
American Chemical Society, Database accession No. 2002:740157 Chemcats, CAS Registry No. 257861–66–8, XP002266175.
American Chemical Society, Database accession No. 2002:740158 Chemcats, CAS Registry No. 257861–68–0, XP002266174.
American Chemical Society, Database accession No. 1973:478762 Caplus, CAS Registry No. 43092–87–1 Caplus, XP002266127.
American Chemical Society, Database accession No. 1957:98876 Caplus, CAS Registry No. 102002–73–3 Caplus, XP002266129.
Catsoulacos, P., "Synthesis of Substituted Dihydrodibenzothiazepines and Related Compounds", Laboratory of Pharmaceutical Chemistry, 1970, 409–411, XP–002268164.
American Chemical Society, Database accession No. 1998:610157 Chemcats, CAS Registry No. 271775–52–1, XP002266301.
American Chemical Society, Database accession No. 1998:610156 Chemcats, CAS Registry No.0271775–51–0, XP002266302.
Catsoulacos, P., "Synthesis of Subsituted Dihydrodibenzothiazepines and Related Compounds", Laboratory of Pharmaceutical Chemistry, 1970, 409–411, XP–002268164.
Chemical Abstracts, vol. 79, No. 13, abstract No.: 78762, XP002266125.
Chemical Abstracts, vol. 93, No. 7, abstract No. 71730, XP002266126.
Chemical Abstracts Serivce Registry Handbook, 2000 Supplement, CAS Registry No. 256285–97–9 through 260528–41–4, XP002266173.
Chemical Abstracts Service Registry Handbook, 2000 Supplement, CAS REgistry No. 271534–00–0 through 276887–31–1, XP002266300.
Connor, et al., "Influence of Substrate Structure on Copper(1)–assisted Cyanide Substitution in Aryl Halides", 1990, J Chem Soc Perkin Trans 1: 1127–32, XP001021533.
International Search Report for PCT US 02/41083, dated Feb. 9, 2004.

(List continued on next page.)

*Primary Examiner*—Zinna Northington Davis
(74) *Attorney, Agent, or Firm*—Senniger Powers

(57) ABSTRACT

The present invention is directed to selective LXR modulators, small molecule compounds corresponding to Formula I and is further directed to a process of treating a condition in a mammal that is modulated by LXR using a therapeutically effective dose of a compound of Formula I.

60 Claims, No Drawings

OTHER PUBLICATIONS

Mounetou et al., "Synthesis of N–[2–(2–Methylpropoxy)Ethyl]–N–(2–[(4–Methoxy)Phenylmethylthio]phenyl)–1–Pyrrolidineethanamine (E)–2–Butenedioate (1:1) Salt (Cerm 12816): A Potential Anti–Aginal Drug", Journal of Labelled Compounds and Radiopharmaceuticals, 1998, 41(3): 181–189, , p. 184 scheme 2, compound 6, XP002266165.

Nandi, et al., "An Unusual Cleavage of a C–S Bond with Concurent S–Arylation Under Palladium–Copper Catalysis", Tetrahedron Letters, 2000, 7259–7262.

Okamoto et al., "A Cholesteryl Ester Transfer Protein Inhibitor Attenuates Atherosclerosis in Rabbits", Nature, 2000, 406: 203–207 XP02266120.

Prasad et al., "Chemistry and Synthesis of Some Dihydro–2H–1,4–Benzothiazine Derivatives", Canadian Journal of Chemistry, 1966, 44:1247–1258, XP001027730.

Protiva, et al., Antihistamin–Substanzen XLV.* Homophenothiazin–Analogon Des Chlorpromazins Und Einige Verwandte Verbindungen, Forshungsinstitut für Pharmazie und Biochemie, Praha, 1958, 207–211, EP–002268156.

Specklin et al., Bull Soc Chim Fr, 1951, 621–626, p. 624 table V, XP000616273.

* cited by examiner

AROMATIC THIOETHER LIVER X-RECEPTOR MODULATORS

REFERENCE TO RELATED APPLICATIONS

This application is a non-provisional application claiming priority from provisional application Ser. No. 60/345,163, filed Dec. 21, 2001, the entire contents of which are hereby incorporated herein by reference in its entirety.

BACKGROUND

Liver X-receptors (LXRs) are nuclear receptors that regulate the metabolism of several important lipids, including cholesterol and bile acids. Most of the cholesterol in plasma is transported on three major lipoprotein classes; VLDL cholesterol (VLDL-C), LDL cholesterol (LDL-C) and HDL cholesterol (HDL-C). Total cholesterol is the sum of all three lipoproteins. Both VLDL-C and LDL-C are associated with atherogenic processes while HDL-C is believed to facilitate cholesterol removal from tissues (e.g. atherosclerotic plaques) and thus have a protective effect on coronary heart disease.

LXR represents a novel intervention point to regulate the reverse cholesterol transport (RCT) pathway, i.e., the removal of cholesterol from peripheral tissues/cells and subsequent uptake via the liver for disposal. Removal of cellular cholesterol requires active transport of free cholesterol across the plasma membrane and onto HDL particles. This transfer of cholesterol from inside the cell and onto HDL in the plasma is mediated by ATP binding cassette 1 (ABCA1) transporter protein. The observation that LXR is a key transcriptional activator of ABCA1 in the macrophage, suggests that induction of LXR will lead to an increase in cholesterol efflux from the macrophage. In addition, it is known that LXR regulates the induction of other genes involved in RCT such as apoE and cholesterol ester transport protein (CETP), suggesting that activating the LXR pathway should also lead to increased uptake of cholesterol by the liver. Thus, activation of LXR by a small molecule ligand will lead to an up-regulation of ABCA1 and induction of the reverse cholesterol transport pathway thereby increasing cholesterol efflux to HDL-C and reducing the cholesterol content of atherosclerotic plaques.

SUMMARY OF THE INVENTION

In general, the present invention is directed to selective LXR modulators, small molecule compounds corresponding to Formula I and the isomers, tautomers, salts and prodrugs thereof:

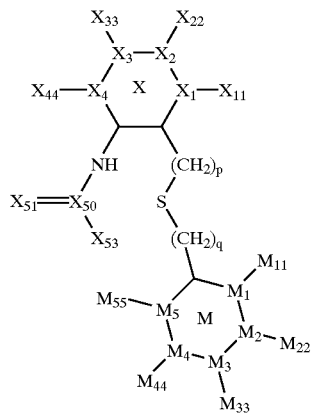

wherein:

the X ring and the M ring are independently aromatic rings;

$M_1$, $M_2$, $M_3$, $M_4$, and $M_5$ are independently a bond, carbon, nitrogen, oxygen or sulfur, provided, however, no more than one of $M_1$, $M_2$, $M_3$, $M_4$, and $M_5$ is a bond;

$M_{11}$, $M_{22}$, $M_{33}$, $M_{44}$, and $M_{55}$ are independently an electron pair, hydrogen, hydrocarbyl, substituted hydrocarbyl, hydroxy, hydrocarbyloxy, substituted hydrocarbyloxy, mercapto, halo, heterocyclo, cyano, nitro, amino, acylamino, acylthio, or acyloxy, or any adjacent two of $M_{11}$, $M_{22}$, $M_{33}$, $M_{44}$, and $M_{55}$ form a fused ring with the atoms of the M ring to which they are bonded; provided, however, $M_{11}$, $M_{22}$, $M_{33}$, $M_{44}$, and $M_{55}$ is not present when $M_1$, $M_2$, $M_3$, $M_4$, or $M_5$, respectively, is a bond;

p and q are independently 0, 1, or 2;

$X_1$, $X_2$, $X_3$, and $X_4$ are independently a bond, carbon, nitrogen, oxygen or sulfur, provided, however, no more than one of $X_1$, $X_2$, $X_3$, and $X_4$ is a bond;

$X_{11}$, $X_{22}$, $X_{33}$, and $X_{44}$ are independently an electron pair, hydrogen, hydrocarbyl, substituted hydrocarbyl, hydroxy, hydrocarbyloxy, substituted hydrocarbyloxy, mercapto, halo, heterocyclo, cyano, nitro, amino, acylamino, acylthio, acyloxy, or acyl; provided, however, $X_{11}$, $X_{22}$, $X_{33}$, or $X_{44}$ is not present when $X_1$, $X_2$, $X_3$ or $X_4$, respectively, is a bond;

$X_{50}$ is carbon, sulfur or sulfoxide, $X_{51}$ is oxygen, sulfur, or $NX_{52}$, $X_{52}$ is hydrogen, hydrocarbyl, or substituted hydrocarbyl; and $X_{53}$ is hydrogen, hydrocarbyl, substituted hydrocarbyl, heterocyclo, or amino.

The present invention is further directed to a process for the treatment or prevention of a condition in a mammal which is modulated by LXR. The process comprises administering to a mammal in need thereof a therapeutically effective dose of a compound of Formula I or an isomer, tautomer, salt or prodrug thereof.

Other aspects of the invention will be in part apparent and in part pointed out hereinafter.

DETAILED DESCRIPTION OF THE PREFERRED EMBODIMENTS

In general, the present invention is directed to small molecule compounds corresponding to Formula I and each of the other formulae disclosed herein, the isomers, tautomers, salts and prodrugs thereof and their use as LXR modulators. In particular, the LXR modulators may be used in the treatment of atherosclerosis, dyslipidemia, diabetes, Alzheimers disease or Niemann-Pick disease.

In one embodiment, the X ring and the M ring of Formula I are independently a six membered aromatic ring such as a benzene, pyridine or pyrimidine ring, or a 5-membered heteroaromatic ring such as a furan, thiophene, oxazole, pyrazole, pyrrole, thiazole, imidazole or isoxazole ring. For example, the X ring may be a 5-membered ring and the M ring may be a 6-membered ring, or vice versa.

In one embodiment, the LXR modulators correspond to Formula II:

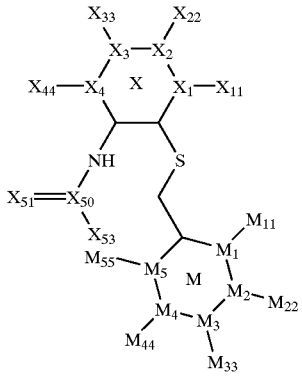

(II)

wherein:

the X ring and the M ring are independently a 6-membered aromatic ring;

$M_1$, $M_2$, $M_3$, $M_4$, and $M_5$ are independently carbon or nitrogen;

$M_{11}$, $M_{22}$, $M_{33}$, $M_{44}$, and $M_{55}$ are independently an electron pair, hydrogen, hydrocarbyl, substituted hydrocarbyl, hydroxy, hydrocarbyloxy, substituted hydrocarbyloxy, mercapto, halo, heterocyclo, cyano, nitro, amino, acylamino, acylthio, or acyloxy, or any adjacent two of $M_{11}$, $M_{22}$, $M_{33}$, $M_{44}$, and $M_{55}$ form a fused ring with the atoms of the M ring to which they are bonded;

$X_1$, $X_2$, $X_3$, and $X_4$ are independently carbon or nitrogen;

$X_{11}$, $X_{22}$, $X_{33}$, and $X_{44}$, are independently an electron pair, hydrogen, hydrocarbyl, substituted hydrocarbyl, hydroxy, hydrocarbyloxy, substituted hydrocarbyloxy, mercapto, halo, heterocyclo, cyano, nitro, amino, acylamino, acylthio, acyloxy or acyl;

$X_{50}$ is carbon, sulfur or sulfoxide;

$X_{51}$ is oxygen, sulfur, or $NX_{52}$;

$X_{52}$ is hydrogen, hydrocarbyl, or substituted hydrocarbyl; and $X_{53}$ is hydrogen, hydrocarbyl, substituted hydrocarbyl, heterocyclo, or amino.

In a further embodiment, the LXR modulators correspond to Formula II wherein the X ring and the M ring are benzene rings. In this embodiment, for example, the compounds correspond to Formula III:

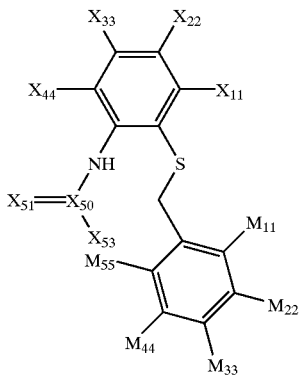

(III)

wherein $X_{11}$, $X_{22}$, $X_{33}$, $X_{44}$, $X_{50}$, $X_{51}$, $X_{53}$, $M_{11}$, $M_{22}$, $M_{33}$, $M_{44}$ and $M_{55}$ are as defined in connection with Formula II. In one embodiment in which the compounds correspond to Formula III, $X_{50}$ is carbon, $X_{51}$ is oxygen, and $X_{53}$ is heterocyclo, optionally substituted alkyl, or optionally substituted phenyl. For example, $X_{53}$ may be heterocyclo (such as thienyl, pyridyl, piperidinyl, piperazinyl, or 2-oxabicyclo [2.2.1]heptane), linear or branched alkyl (such as methyl, t-butyl, isopropyl, or isobutyl), substituted alkyl (such as trichloromethyl, trifluoromethyl, $(CH_2Cl)(CH_3)_2C-$, $(CH_3C(O)OCH_2)(CH_3)_2C-$, or $(CH_2OH)(CH_3)_2C-$), cycloalkyl (such as cyclohexyl, cyclopentyl, adamantyl, or methylcyclohexane), phenyl, or substituted phenyl (such as 3-chlorophenyl or methoxyphenyl). In addition, in each of the embodiments in which the compounds correspond to Formula III, one of $X_{11}$, $X_{22}$, $X_{33}$, and $X_{44}$ may be hydrogen, alkyl (such as methyl), nitro, or halo (such as chloro or fluoro) while the remainder of $X_{11}$, $X_{22}$, $X_{33}$, $X_{44}$ are hydrogen. In addition, in each of the embodiments in which the compounds correspond to Formula III, $M_{11}$ and $M_{22}$, $M_{22}$ and $M_{33}$, $M_{33}$ and $M_{44}$, or $M_{44}$ and $M_{55}$, and the atoms of the M ring to which they are attached may form a fused ring comprising $-O-CH_2-O-CH_2-$ or $-OCH_2O-$ while the others of $M_{11}$, $M_{22}$, $M_{33}$, $M_{44}$ and $M_{55}$ may be hydrogen, halogen (such as chloro or fluoro), or nitro; alternatively, (i) any two of $M_{11}$, $M_{22}$, $M_{33}$, $M_{44}$ and $M_{55}$ may be alkoxy (such as methoxy) while the others are hydrogen, (ii) one of $M_{11}$, $M_{22}$, $M_{33}$, $M_{44}$ and $M_{55}$ may be alkoxy (such as methoxy), one of $M_{11}$, $M_{22}$, $M_{33}$, $M_{44}$ and $M_{55}$ may be nitro or alkyl (such as methyl) while the others are hydrogen, or (iii) one of $M_{11}$, $M_{22}$, $M_{33}$, $M_{44}$ and $M_{55}$ may be alkyl (such as methyl) or substutited alkyl (such as chloro, dichloro or trichloromethyl or fluoro, difluoro or trifluoromethyl), or alkoxy (such as methoxy) while the others are hydrogen.

In a further embodiment, the LXR modulators correspond to Formula II wherein the X ring is a benzene ring and the M ring is a pyridine ring. In yet another embodiment, the X ring is a benzene ring and the M ring is a pyrimidine ring. In each of these embodiments, $X_{11}$, $X_{22}$, $X_{33}$, $X_{44}$, $X_{50}$, $X_{51}$, $X_{53}$, $M_{11}$, $M_{22}$, $M_{33}$, $M_{44}$ and $M_{55}$ are as defined in connection with Formula II or Formula III.

In another embodiment, the LXR modulators correspond to Formula IV:

(IV)

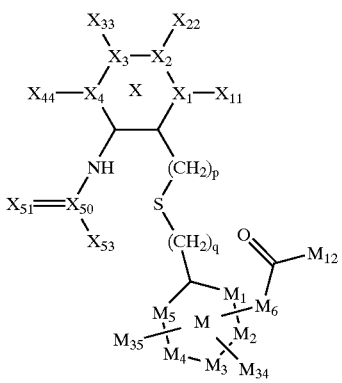

wherein
the X ring and the M ring are independently aromatic rings;

$M_1$, $M_2$, $M_3$, $M_4$, and $M_5$ are independently a bond, carbon, nitrogen, oxygen or sulfur, provided, however, no more than one of $M_1$, $M_2$, $M_3$, $M_4$, and $M_5$ is a bond;

$M_6$ is hydrocarbyl, substituted hydrocarbyl or amino;

$M_{12}$ is hydrocarbyl, substituted hydrocarbyl, hydroxy, hydrocarbyloxy, substituted hydrocarbyloxy, hydrocarbylthio, substituted hydrocarbylthio or amino;

$M_{34}$ and $M_{35}$ are independently an electron pair, hydrogen, hydrocarbyl, substituted hydrocarbyl, hydroxy, hydrocarbyloxy, substituted hydrocarbyloxy, mercapto, halo, heterocyclo, cyano, nitro, amino, acylamino, acylthio, or acyloxy, or $M_{34}$ and $M_{35}$ are attached to adjacent atoms and form a fused ring with the atoms of the M ring to which they are bonded;

p and q are independently 0, 1, or 2;

$X_1$, $X_2$, $X_3$, and $X_4$ are independently a bond, carbon, nitrogen, oxygen or sulfur, provided, however, no more than one of $X_1$, $X_2$, $X_3$, and $X_4$ is a bond;

$X_{11}$, $X_{22}$, $X_{33}$, and $X_{44}$, are independently an electron pair, hydrogen, hydrocarbyl, substituted hydrocarbyl, hydroxy, hydrocarbyloxy, substituted hydrocarbyloxy, mercapto, halo, heterocyclo, cyano, nitro, amino, acylamino, acylthio, acyloxy, or acyl; provided, however, $X_{11}$, $X_{22}$, $X_{33}$, or $X_{44}$ is not present when $X_1$, $X_2$, $X_3$ or $X_4$, respectively, is a bond;

$X_{50}$ is carbon, sulfur or sulfoxide, $X_{51}$ is oxygen, sulfur, or $NX_{52}$, $X_{52}$ is hydrogen, hydrocarbyl, or substituted hydrocarbyl; and $X_{53}$ is hydrogen, hydrocarbyl, substituted hydrocarbyl, heterocyclo, or amino.

In one embodiment in which the LXR modulators correspond to Formula IV, the X ring and the M ring are independently a benzene, pyridine or pyrimidine ring and the sum of p and q is one. In another embodiment in which the LXR modulators correspond to Formula IV, the X ring and the M ring are independently a benzene or pyridine ring, $X_{50}$ is carbon, $X_{51}$ is oxygen and the sum of p and q is one. In another embodiment in which the LXR modulators correspond to Formula IV, the X ring and the M ring are each benzene rings and the sum of p and q is one. In another embodiment in which the LXR modulators correspond to Formula IV, the X ring and the M ring are each benzene rings, $X_{50}$ is carbon, $X_{51}$ is oxygen, and the sum of p and q is one. In a further embodiment in which the LXR modulators correspond to Formula IV, the X ring and the M ring are benzene rings, p is zero and q is one. In a further embodiment in which the LXR modulators correspond to Formula IV, the X ring and the M ring are benzene rings, $X_{50}$ is carbon, $X_{51}$ is oxygen, p is one and q is zero. In a further embodiment in which the LXR modulators correspond to Formula IV, the X ring and the M ring are benzene rings, $X_{50}$ is carbon, $X_{51}$ is oxygen, p is zero and q is one. In each of these separate embodiments in which the LXR modulators correspond to Formula IV, $X_{53}$ may be heterocyclo (such as thienyl, pyridyl, piperidinyl, piperazinyl, or 2-oxabicyclo [2.2.1]heptane), linear or branched alkyl (such as methyl, t-butyl, isopropyl, or isobutyl), substituted alkyl (such as trichloromethyl, trifluoromethyl, $(CH_2Cl)(CH_3)_2C$—, $(CH_3C(O)OCH_2)(CH_3)_2C$—, or $(CH_2OH)(CH_3)_2C$—), cycloalkyl (such as cyclohexyl, cyclopentyl, adamantyl, or methylcyclohexane), phenyl, or substituted phenyl such as 3-chlorophenyl or methoxyphenyl. In addition, in each of these separate embodiments, one of $X_{11}$, $X_{22}$, $X_{33}$, $X_{44}$ may be hydrogen, alkyl (such as methyl), nitro, or halo (such as chloro or fluoro) while the remainder of $X_{11}$, $X_{22}$, $X_{33}$, $X_{44}$ are hydrogen. In addition, in each of these separate embodiments, $M_{12}$ may be optionally substituted alkoxy, optionally substituted alkylthio, optionally substituted alkylamino, or optionally substituted hydrocarbyl.

In a further embodiment, the LXR modulators correspond to Formula V:

(V)

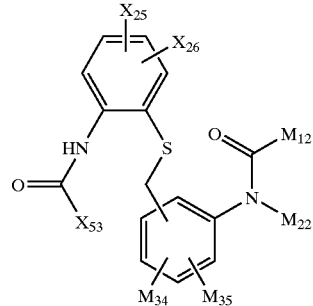

wherein
$X_{25}$ and $X_{26}$ are independently hydrogen, hydrocarbyl, substituted alkyl, nitro or halo, $M_{12}$ is alkoxy, alkylthio, amino, hydrocarbyl or substituted hydrocarbyl;

$M_{22}$ is hydrogen, hydrocarbyl or substituted hydrocarbyl;

$M_{34}$ and $M_{35}$ are independently hydrogen, alkyl, substituted alkyl, halogen, or nitro, or are attached to adjacent carbon atoms and, in combination with these adjacent carbon atoms, define a fused ring; and $X_{53}$ is hydrocarbyl, substituted hydrocarbyl or heterocyclo.

For example, $X_{25}$ and $X_{26}$ independently may be hydrogen, methyl, nitro, chloro or fluoro, $M_{12}$ may be methoxy, alkylthio, alkyl or substituted alkyl, and $M_{34}$ and $M_{35}$ independently may be hydrogen, alkyl, substituted alkyl, chloro, fluoro, or nitro. By way of further example, $M_{34}$ and $M_{35}$ may be attached to adjacent carbon atoms and, in combination with these adjacent carbon atoms define a fused ring. By way of further example, in each of these separate embodiments in which the compound corresponds to Formula V, $X_{53}$ may be heterocyclo (such as thienyl, pyridyl, piperidinyl, piperazinyl, 2-oxabicyclo[2.2.1]heptane), linear or branched alkyl (such as methyl, t-butyl, isopropyl, or isobutyl), substituted alkyl (such as trichloromethyl, trifluoromethyl, $(CH_2Cl)(CH_3)_2C$—, $(CH_3C(O)OCH_2)$ $(CH_3)_2C$—, or $(CH_2OH)(CH_3)_2C$—), cycloalkyl (such as cyclohexyl, cyclopentyl, adamantyl, or methylcyclohexane), phenyl, or substituted phenyl (such as 3-chlorophenyl or methoxyphenyl). By way of further example, in each of these separate embodiments in which the compound corresponds to Formula V, one of $X_{25}$ and $X_{26}$ may be hydrogen and/or one of $M_{34}$ and $M_{35}$ may be hydrogen.

In a further embodiment, the LXR modulators correspond to Formula VI:

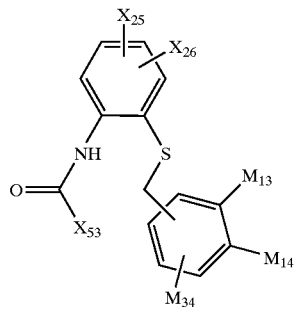

(VI)

wherein:

$M_{13}$ and $M_{14}$ and the carbon atoms to which they are attached define a five or six-membered fused ring;

$X_{25}$ and $X_{26}$ are independently hydrogen, alkyl, substituted alkyl, nitro or halo, $M_{34}$ is hydrogen, alkyl, substituted alkyl, halogen, or nitro; and $X_{53}$ is hydrocarbyl, substituted hydrocarbyl or heterocyclo.

For example, in one embodiment in which the compounds correspond to structure VI, the ring atoms are selected from carbon, nitrogen, oxygen and sulfur. For example the five or six-membered fused ring incorporating $M_{13}$ and $M_{14}$ may comprise —O—$CH_2$—O—$CH_2$— when the ring is a six membered ring, or —O—$CH_2$—O— when the ring is a five membered ring. In each of these and other embodiments in which the compounds correspond to structure VI, $X_{25}$ and $X_{26}$ independently may be hydrogen, methyl, nitro, chloro or fluoro, and $M_{34}$ may be hydrogen, alkyl, substituted alkyl, chloro, fluoro, or nitro. By way of further example, in each of these separate embodiments in which the compound corresponds to Formula VI, $X_{53}$ may be heterocyclo (such as thienyl, pyridyl, piperidinyl, piperazinyl, 2-oxabicyclo [2.2.1]heptane), linear or branched alkyl (such as methyl, t-butyl, isopropyl, or isobutyl), substituted alkyl (such as trichloromethyl, trifluoromethyl, ($CH_2Cl$)($CH_3$)$_2C$—, ($CH_3C(O)OCH_2$)($CH_3$)$_2C$—, or ($CH_2OH$)($CH_3$)$_2C$—), cycloalkyl (such as cyclohexyl, cyclopentyl, adamantyl, or methylcyclohexane), phenyl, or substituted phenyl (such as 3-chlorophenyl or methoxyphenyl). By way of further example, in each of these separate embodiments in which the compound corresponds to Formula VI, one of $X_{25}$ and $X_{26}$ may be hydrogen.

In another embodiment, the LXR modulators correspond to Formula VII:

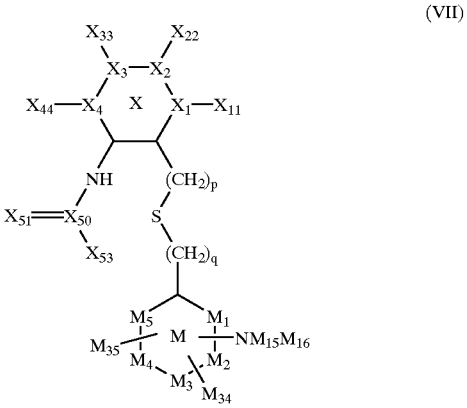

(VII)

wherein the X ring and the M ring are independently aromatic rings;

$M_1$, $M_2$, $M_3$, $M_4$, and $M_5$ are independently a bond, carbon, nitrogen, oxygen or sulfur, provided, however, no more than one of $M_1$, $M_2$, $M_3$, $M_4$, and $M_5$ is a bond;

$M_{15}$ and $M_{16}$ are independently hydrogen, hydrocarbyl, substituted hydrocarbyl, acyl, or heterocyclo, provided $M_{15}$ and $M_{16}$ are not each acyl;

$M_{34}$ and $M_{35}$ are independently an electron pair, hydrogen, hydrocarbyl, substituted hydrocarbyl, hydroxy, hydrocarbyloxy, substituted hydrocarbyloxy, mercapto, halo, heterocyclo, cyano, nitro, amino, acylamino, acylthio, or acyloxy, or $M_{34}$ and $M_{35}$ are bonded to adjacent atoms and form a fused ring with the atoms of the M ring to which they are bonded;

p and q are independently 0, 1, or 2;

$X_1$, $X_2$, $X_3$, and $X_4$ are independently a bond, carbon, nitrogen, oxygen or sulfur, provided, however, no more than one of $X_1$, $X_2$, $X_3$, and $X_4$ is a bond;

$X_{11}$, $X_{22}$, $X_{33}$, and $X_{44}$, are independently an electron pair, hydrogen, hydrocarbyl, substituted hydrocarbyl, hydroxy, hydrocarbyloxy, substituted hydrocarbyloxy, mercapto, halo, heterocyclo, cyano, nitro, amino, acylamino, acylthio, acyloxy, or acyl; provided, however, $X_{11}$, $X_{22}$, $X_{33}$, or $X_{44}$ is not present when $X_1$, $X_2$, $X_3$ or $X_4$, respectively, is a bond;

$X_{50}$ is carbon, sulfur or sulfoxide, $X_{51}$ is oxygen, sulfur, or $NX_{52}$, $X_{52}$ is hydrogen, hydrocarbyl, or substituted hydrocarbyl; and $X_{53}$ is hydrogen, hydrocarbyl, substituted hydrocarbyl, heterocyclo, or amino.

In one embodiment in which the LXR modulators correspond to Formula VII, the X ring and the M ring are independently benzene or pyridine rings and the sum of p and q is one. In another embodiment in which the LXR modulators correspond to Formula VII, the X ring and the M ring are independently benzene or pyridine rings, $X_{50}$ is carbon, $X_{51}$ is oxygen and the sum of p and q is one. In another embodiment in which the LXR modulators correspond to Formula VII, the X ring and the M ring are benzene rings and the sum of p and q is one. In another embodiment in which the LXR modulators correspond to Formula VII, the X ring and the M ring are benzene rings, $X_{50}$ is carbon, $X_{51}$ is oxygen, and the sum of p and q is one. In a further embodiment in which the LXR modulators correspond to Formula VII, the X ring and the M ring are benzene rings, p is zero and q is one. In a further embodiment in which the LXR modulators correspond to Formula VII, the X ring and the M ring are benzene rings, $X_{50}$ is carbon, $X_{51}$ is oxygen, p is zero and q is one. In general, in each of these separate embodiments in which the LXR modulators correspond to Formula VII, $X_{11}$, $X_{22}$, $X_{33}$, $X_{44}$, $X_{53}$, $M_{34}$ and $M_{35}$ are as defined in connection with Formula VII. Optionally, in each of these embodiments in which the LXR modulator corresponds to Formula VII, $X_{53}$ may be heterocyclo (such as thienyl, pyridyl, piperidinyl, piperazinyl, or 2-oxabicyclo[2.2.1]heptane), linear or branched alkyl (such as methyl, t-butyl, isopropyl, or isobutyl), substituted alkyl (such as trichloromethyl, trifluoromethyl, $(CH_2Cl)(CH_3)_2C-$, $(CH_3C(O)OCH_2)(CH_3)_2C-$, or $(CH_2OH)(CH_3)_2C-$), cycloalkyl (such as cyclohexyl, cyclopentyl, adamantyl, or methylcyclohexane), phenyl, or substituted phenyl (such as 3-chlorophenyl or methoxyphenyl). In addition, in each of these separate embodiments in which the LXR modulator corresponds to Formula VII, one of $X_{11}$, $X_{22}$, $X_{33}$, $X_{44}$ may be hydrogen, alkyl (such as methyl), nitro, or halo (such as chloro or fluoro) while the remainder of $X_{11}$, $X_{22}$, $X_{33}$, $X_{44}$ may be hydrogen.

In one embodiment in which the compounds correspond to Formula VII, $M_{15}$ is hydrogen and $M_{16}$ is $-C(=O)M_{17}$ wherein $M_{17}$ is hydrocarbyl, substituted hydrocarbyl, hydrocarbyloxy, substituted hydrocarbyloxy, or heterocyclo. In this embodiment, $X_{11}$, $X_{22}$, $X_{33}$, $X_{44}$, $X_{53}$, $M_{34}$ and $M_{35}$ are as previously in each of the separate embodiments defined in connection with Formula VII.

In a further embodiment, the LXR modulators correspond to Formula VIII:

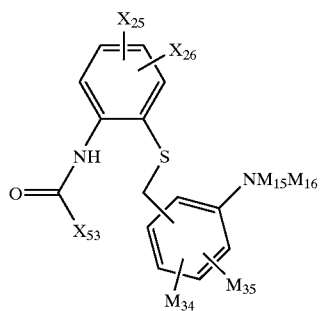

(VIII)

wherein:

$M_{15}$ and $M_{16}$ are independently hydrogen, hydrocarbyl, substituted hydrocarbyl, or acyl (provided $M_{15}$ and $M_{16}$ are not each acyl), and $X_{25}$, $X_{26}$, $X_{53}$, $M_{34}$ and $M_{35}$ are as previously defined in connection with Formula VII. In one embodiment in which the LXR modulator corresponds to Formula VIII, $X_{25}$ and $X_{26}$ are independently hydrogen, alkyl (such as methyl), nitro, or halo (such as chloro or fluoro), $M_{34}$ and $M_{35}$ are independently hydrogen, alkyl, substituted alkyl, halogen (such as chloro or fluoro), or nitro; $X_{53}$ may be heterocyclo (such as thienyl, pyridyl or 2-oxabicyclo[2.2.1]heptane), linear or branched alkyl (such as methyl, t-butyl, isopropyl, or isobutyl), substituted alkyl (such as trichloromethyl, trifluoromethyl, $(CH_2Cl)(CH_3)_2C-$, $(CH_3C(O)OCH_2)(CH_3)_2C-$, or $(CH_2OH)(CH_3)_2C-$), cycloalkyl (such as cyclohexyl, cyclopentyl, adamantyl, or methylcyclohexane), phenyl, or substituted phenyl (such as 3-chlorophenyl or methoxyphenyl). By way of further example, in each of these separate embodiments in which the compound corresponds to Formula VIII, one of $X_{25}$ and $X_{26}$ may be hydrogen and/or one of $M_{34}$ and $M_{35}$ may be hydrogen.

Another aspect of the present invention are the prodrugs of the compounds corresponding to the formulae disclosed herein, which are converted under physiological conditions to the biologically active drug by any of a number of chemical and biological mechanisms. In general terms, these prodrug conversion mechanisms are hydrolysis, reduction, oxidation, and elimination.

A further aspect of the invention encompasses conversion of the prodrug to the biologically active drug by elimination of the prodrug moiety. Generally speaking, in this embodiment the prodrug moiety is removed under physiological conditions with a chemical or biological reaction. The elimination results in removal of the prodrug moiety and liberation of the biologically active drug. Any compound of the present invention corresponding to any of the formulas disclosed herein may undergo any combination of the above detailed mechanisms to convert the prodrug to the biologically active compound. For example, a particular compound may undergo hydrolysis, oxidation, elimination, and reduction to convert the prodrug to the biologically active compound. Equally, a particular compound may undergo only one of these mechanisms to convert the prodrug to the biologically active compound.

The compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of any of the formulae disclosed herein. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures or R and S forms for each stereocenter present.

Also included in the present invention are the pharmaceutically acceptable salts of any compound having corresponding to any of the formulas disclosed herein and the isomers, tautomers, and prodrugs thereof. The term "pharmaceutically-acceptable salt" includes commonly used to form alkali metal salts and to form addition salts of free acids or free bases. The nature of the salt is not critical, provided that it is pharmaceutically acceptable. Suitable pharmaceutically acceptable acid addition salts of the compounds may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, and galacturonic acid. Suitable pharmaceutically-acceptable base addition salts of the compounds include metallic salts made from aluminum, calcium, lithium, magnesium, potassium, sodium and zinc or organic salts made from N,N'-dibenzylethyleneldiamine, choline, chloroprocaine, diethanolamine, ethylenediamine, meglumine (N-methylglucamine) and procain. All of these salts may be prepared by conventional means from the corresponding compound by reacting, for example, the appropriate acid or base with the selected compound of any of the formulae disclosed herein or the prodrug, isomer, or tautomer thereof.

The present invention also comprises a pharmaceutical composition comprising a therapeutically effective amount of the compound of the invention in association with at least one pharmaceutically acceptable carrier, adjuvant or diluent. Pharmaceutical compositions of the present invention can comprise the active compounds of any of the formulae disclosed herein or the prodrug, isomer, tautomer or prodrug thereof in association with one or more non-toxic, pharmaceutically-acceptable carriers and/or diluents and/or adjuvants (collectively referred to herein as "carrier" materials) and, if desired, other active ingredients. The compostions of the present invention may be administered by any suitable route, preferably in the form of a pharmaceutical composition adapted to such a route, and in a dose effective for the treatment intended.

Synthesis

As depicted in the schemes below, compounds of the present invention can be prepared by alkylation of (i) to give an amine (iii) which can undergo acylation with an acid chloride or anhydride to give the target compounds (iv). Additional compounds can be prepared by tin chloride reduction of (v) to give (vi) which can undergo reductive alkylation to form (vii) or coupling to an acid chloride or anhydride to give (viii).

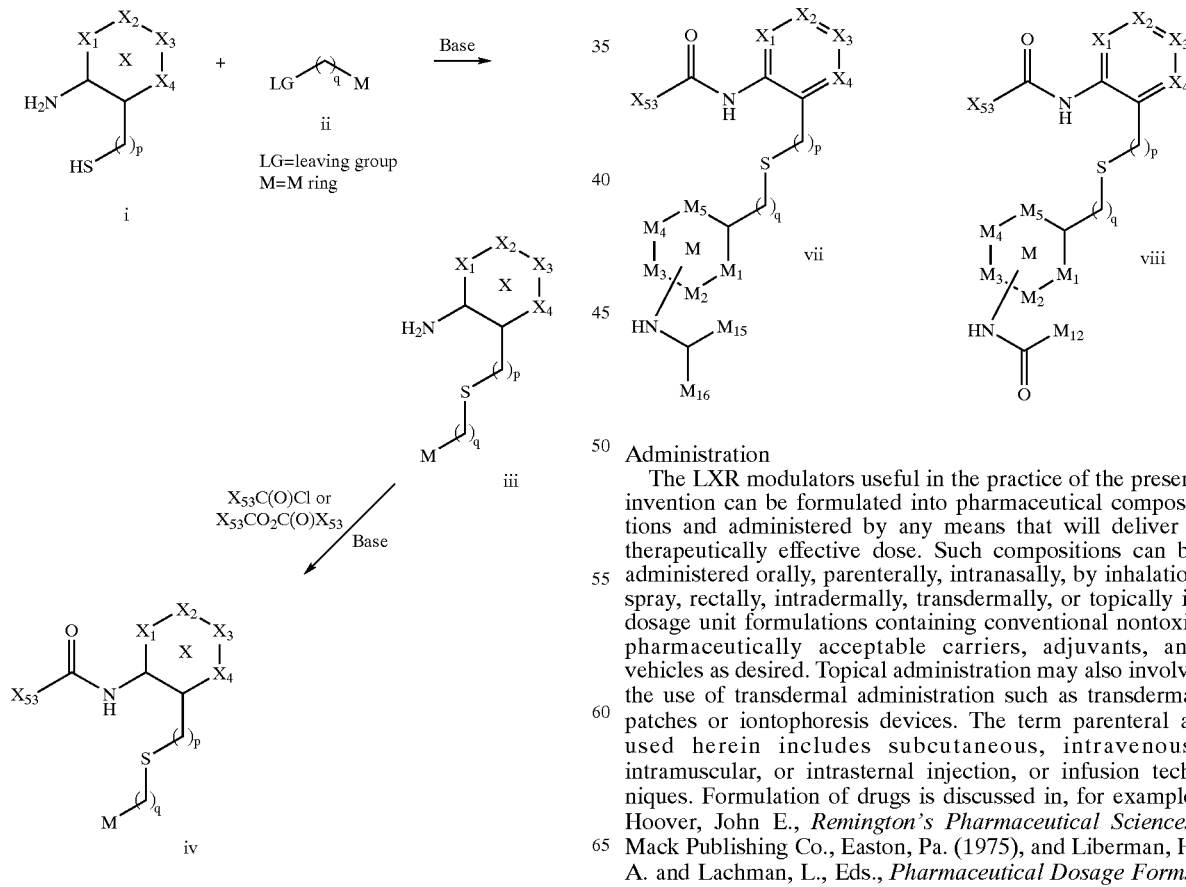

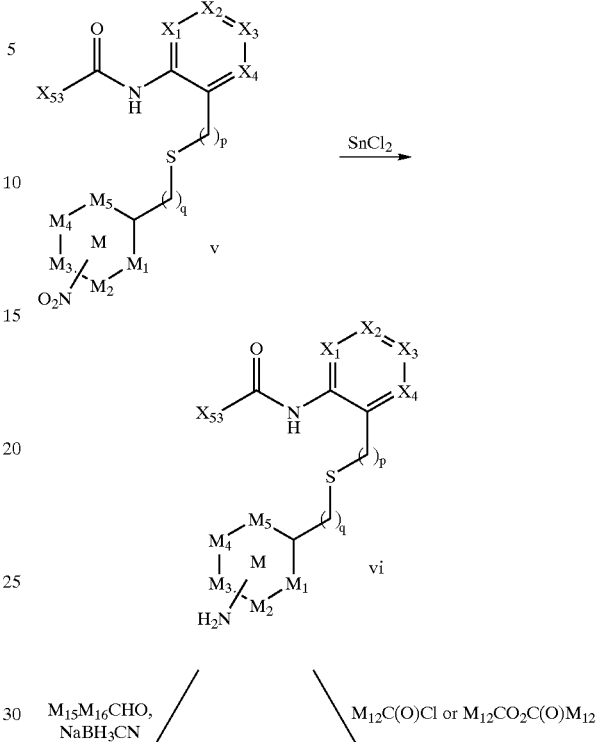

Administration

The LXR modulators useful in the practice of the present invention can be formulated into pharmaceutical compositions and administered by any means that will deliver a therapeutically effective dose. Such compositions can be administered orally, parenterally, intranasally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., *Remington's Pharmaceutical Sciences*, Mack Publishing Co., Easton, Pa. (1975), and Liberman, H. A. and Lachman, L., Eds., *Pharmaceutical Dosage Forms*, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage of the LXR modulator will vary depending upon the patient and the particular mode of administration. In general, the pharmaceutical compositions may contain a LXR modulator in the range of about 1 and 2500 mg, more typically, in the range of about 5 and 1000 mg and still more typically, between about 10 and 500 mg. A daily dose of about 0.1 to 50 mg/kg body weight, or more typically, between about 0.1 and about 25 mg/kg body weight and even more typically, from about 0.5 to 10 mg/kg body weight, may be appropriate. The daily dose can be administered in one to about four doses per day. Those skilled in the art will appreciate that dosages may also be determined with guidance from Goodman & Goldman's *The Pharmacological Basis of Therapeutics*, Ninth Edition (1996), Appendix II, pp. 1707–1711 and from Goodman & Goldman's *The Pharmacological Basis of Therapeutics*, Tenth Edition (2001), Appendix II, pp.475–493.

Definitions

The term "acyl," as used herein alone or as part of another group, denotes the moiety formed by removal of the hydroxyl group from the —COOH group of an organic carboxylic acid, e.g., RC(O)— wherein R is $R_a$, $R_aO$—, $R_aS$—, or $R_aR_bN$—, $R_a$ and $R_b$ are independently hydrogen, hydrocarbyl, substituted hydrocarbyl, or heterocyclo and "—" denotes the point of attachment.

The term "acylamino," as used herein alone or as part of another group, denotes an acyl group as defined above, bonded through a nitrogen atom, e.g., $RC(O)N(R_c)$— wherein R is as defined in connection with the term "acyl", $R_c$ is hydrogen, hyrocarbyl, or substituted hydrocarbyl, and "—" denotes the point of attachment.

The term "acyloxy" as used herein alone or as part of another group, denotes an acyl group as defined above, bonded through an oxygen atom (—O—), e.g., RC(O)O— wherein R is as defined in connection with the term "acyl" and "—" denotes the point of attachment.

The term "acylthio" as used herein alone or as part of another group, denotes an acyl group as defined above, bonded through a sulfur atom (—S—), e.g., RC(O)S— wherein R is as defined in connection with the term "acyl" and "—" denotes the point of attachment.

The term "amino" as used herein alone or as part of another group shall denote a primary, secondary or tertiary amine which may optionally be hydrocarbyl, substituted hydrocarbyl or heteroatom substituted. Specifically included are secondary or tertiary amine nitrogens which are members of a heterocyclic ring. Also specifically included, for example, are secondary or tertiary amino groups substituted by an acyl moiety.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" shall mean aryl or heteroaromatic.

The terms "aryl" or "ar" as used herein alone or as part of another group denote optionally substituted carbocyclic aromatic groups, preferably monocyclic or bicyclic groups containing from 6 to 12 carbon atoms in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroaromatic" as used herein alone or as part of another group denote optionally substituted aromatic groups having at least one carbon atom and at least a heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrazolyl, pyrrolyl, indolyl, quinolinyl, thiazolyl, isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic, cyclic or aryl hydrocarbon groups, such as alkaryl, alkenaryl and alkynaryl. Unless otherwise indicated, these moieties preferably comprise 1 to 20 carbon atoms.

The "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. For example, substituents include moieties in which a carbon atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The following examples illustrate the invention.

EXAMPLE 1

N-(2-{[(6-chloro-1,3-benzodioxol-5-yl)methyl]thio}phenyl)thiophene-2-carboxamide

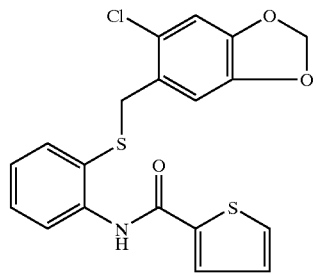

2-aminothiophenol (0.4 mmol) and PS-DIEA resin (0.35 g, 3.76 mmol/g) were combined in dichloromethane (4 mL) and agitated for 10 min. 5-chloro-6-(chloromethyl)-1,3-benzodioxole (0.3 mmol) was added and the reaction agitated for a further 3 h. Reaction was treated with MP $BH_4^-$ resin (Argonaut 3.16 mmol/g) for 2 h then filtered.

The filtrate was combined with triethylamine (0.1 mL) and thiophene-2-carbonyl chloride (0.4 mmol) and agitated for 18 h. The solvent was removed under a stream of nitrogen and the residue was purified by reverse phase chromatography to give the title product. $^1$H NMR (CDCl$_3$) δ 9.02 (s, 1 H), 8.45 (dd, 1 H), 7.60 (dd, 1 H), 7.55 (dd, 1 H), 7.51 (dd, 1 H), 7.42–7.39 (m, 1 H), 7.14 (dd, 1 H), 7.12–7.08 (m, 1 H), 6.51 (s, 1 H), 6.13 (s, 1 H), 5.85 (s, 2 H), 3.90 (s, 2 H); MS (ESI+) for $C_{19}H_{14}ClNO_3S_2$ m/z 404 (M+H)$^+$.

EXAMPLE 2

N-{2-[(2-methoxy-5-nitrobenzyl)thio]phenyl}thiophene-2-carboxamide

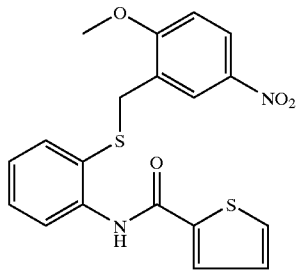

Prepared in the manner of Example 1, except 2-(bromomethyl)-1-methoxy-4-nitrobenzene was substituted for 5-chloro-6-(chloromethyl)-1,3-benzodioxole and the compound was purifed by trituration with methanol. $^1$H NMR (CDCl$_3$) δ 9.10 (s, 1 H), 8.42 (dd, 1 H), 7.98 (dd, 1 H), 7.80 (d, 1 H), 7.55 (dd, 1 H), 7.51 (dd, 1 H), 7.48 (dd, 1 H), 7.40–7.35 (m, 1 H), 7.10 (dd, 1 H), 7.08–7.03 (m, 1 H), 6.67 (d, 1 H), 3.97 (s, 2 H), 3.59 (s, 3 H); MS (ESI+) for $C_{19}H_{16}N_2O_4S_2$ m/z 401 (M+H)$^+$.

EXAMPLE 3

N-{2-[(2-methoxybenzyl)thio]phenyl}thiophene-2-carboxamide

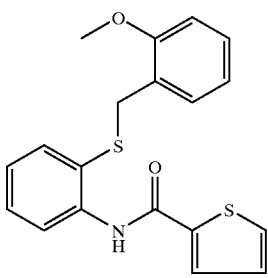

Prepared in the manner of Example 1, except that 1-(bromomethyl)-2-methoxybenzene was substituted for 5-chloro-6-(chloromethyl)-1,3-benzodioxole. $^1$H NMR (CDCl$_3$) δ 9.21 (s, 1 H), 8.47 (dd, 1 H), 7.55–7.51 (m, 2 H), 7.42 (1, 1 H), 7.39–7.34 (m, 1 H), 7.11–7.01 (m, 3 H), 6.79 (dd, 1 H), 6.70–6.63 (m, 2 H), 3.95 (s, 2 H), 3.62 (s, 3 H); MS (ESI+) for C$_{19}$H$_{17}$NO$_2$S$_2$ m/z 356 (M+H)$^+$.

EXAMPLE 4

N-(2-{[(6-chloro-1,3-benzodioxol-5-yl)methyl]thio}phenyl)acetamide

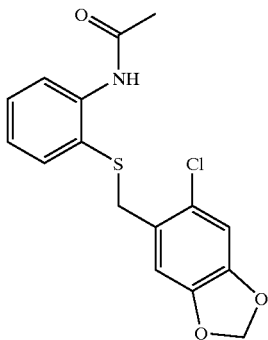

2-aminothiophenol (0.4 mmol) and PS-DIEA resin (0.35 g, 3.76 mmol/g) were combined in dichloromethane (4 mL) and agitated for 10 min. 5-chloro-6-(chloromethyl)-1,3-benzodioxole (0.3 mmol) was added and the reaction agitated for a further 3 h. Reaction was treated with MP BH$_4^-$ resin (Argonaut 3.16 mmol/g) for 2 h then filtered. The filtrate was combined with triethylamine (0.4 mmol), PS-DMAP resin (0.1 g) and acetyl chloride (0.4 mmol). Agitate for 18 h then treat the reaction with PS-trisamine resin for 4 h, filter and remove the solvent under a stream of nitrogen. The residue was purified by reverse phase chromatography. $^1$H NMR (CDCl$_3$) δ 8.38–8.32 (m, 2 H), 7.52 (m, 1 H), 7.38–7.32 (m, 1 H), 7.07–7.02 (m, 1 H), 6.83 (s, 1 H), 6.25 (s, 1 H), 5.93 (s, 2 H), 3.90 (s, 2 H), 2.09 (s, 3 H);MS (ESI+) for C$_{16}$H$_{14}$ClNO$_3$S m/z 336 (M+H)$^+$.

EXAMPLE 5

N-(2-{[(6-chloro-1,3-benzodioxol-5-yl)methyl]thio}phenyl)-2,2,2-trifluoroacetamide

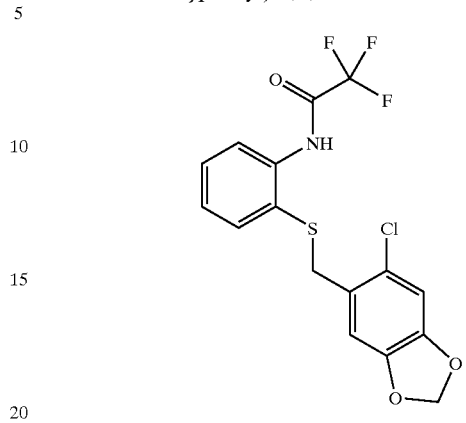

Prepared in the manner of Example 4, except trifluoroacetic acid anhydride was substituted for acetyl chloride. $^1$H NMR (CDCl$_3$) δ 9.24 (s, 1 H), 8.34 (dd, 1 H), 7.62 (dd, 1 H), 7.46–7.40 (m, 1 H), 7.22–7.18 (m, 1 H), 6.80 (s, 1 H), 6.21 (s, 1 H), 5.91 (s, 2 H), 3.92 (s, 2 H);MS (ESI+) for C$_{16}$H$_{11}$ClF$_3$NO$_3$S m/z 389 (M+H)$^+$.

EXAMPLE 6

N-(2-{[(6-chloro-4H-1,3-benzodioxin-8-yl)methyl]thio}phenyl)-2,2-dimethylpropanamide

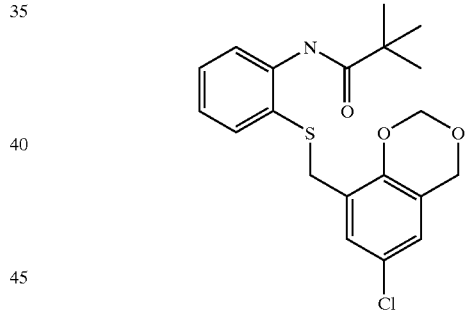

Step 1

2-{[(6-chloro-4H-1,3-benzodioxin-8-yl)methyl]thio}aniline hydrochloride 2-aminothiophenol (1.25 g, 10 mmol), 6-chloro-8-(chloromethyl)-4H-1,3-benzodioxine (2.17 g, 10 mmol) and potassium carbonate (4.10 g, 30 mmol) were combined in absolute ethanol (100 mL) and stirred 18 h. Dilute with ethyl acetate and wash with saturated sodium bicarbonate solution then brine. The solution was dried over sodium sulfate and the solvent removed in vacuo. The residue was dissolved in methanol and treated with MP BH$_4^-$ resin (Argonaut 3.16 mmol/g) and potassium carbonate for 48 h. The mixture was filtered and the solvent removed in vacuo. The resulting oil was dissolved in dichloromethane and passed through a 5 g plug of silica gel. The solvent was removed in vacuo and the residue was precipitated from diethyl ether with a solution of hydrogen chloride in dioxane to give the product as an off white powder, 2.52 g (74%). MS (ESI+) for C$_{15}$H$_{14}$ClNO$_2$S m/z 308 (M+H)$^+$.

Step 2

N-(2-{[(6-chloro-4H-1,3-benzodioxin-8-yl)methyl]thio}phenyl)-2,2-dimethylpropanamide The product from step 1 (75 mg, 0.22 mmol) was dissolved in a mixture of dichloromethane and diisopropyl ethyl amine (4 mL, ~40:1), PS DMAP resin (0.10 g, Argonaut 1.41 mmol/g) was added in followed by 2,2-dimethylpropanoyl chloride (0.15 mL, 1.25 mmol). The reaction was agitated for 24 hours and then treated with PS trisamine (Argonaut 4.27 mmol/g) for 6 h filtered and the solvent removed under a stream of nitrogen. The residue was chromatographed on silica to give the title product 55 mg (65%). $^1$H NMR (CDCl$_3$) δ 9.87 (s, 1 H), 8.45 (dd, 1 H), 7.39 (dd, 1 H), 7.33 (dt, 1 H), 7.00 (dt, 1 H), 6.80 (dd, 2 H), 4.98 (s, 2 H), 4.77 (s, 2 H), 3.84 (s, 2 H), 1.28 (s, 9 H); MS (ESI+) for C$_{20}$H$_{22}$ClNO$_3$S m/z 392 (M+H)$^+$.

EXAMPLE 7

N-(2-{[(6-chloro-4H-1,3-benzodioxin-8-yl)methyl]thio}phenyl)-2-methylpropanamide

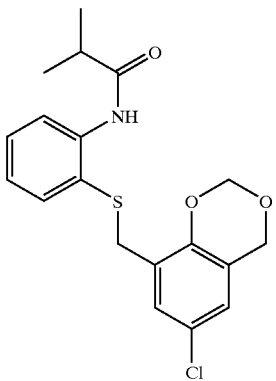

Prepared in the manner of Example 6, step 2, except 2-methylpropanoyl chloride was substituted for 2,2-dimethylpropanoyl chloride. $^1$H NMR (CDCl$_3$) δ 8.51 (s, 1 H), 8.42 (dd, 1 H), 7.41 (dd, 1 H), 7.37–7.31 (m, 1 H), 6.82 (m, 2 H), 5.0 (s, 2 H), 4.78 (s, 2 H), 3.83 (s, 2 H), 2.50–2.42 (m, 1 H), 1.25 (s, 3 H), 1.22 (s, 3 H); MS (ESI+) for C$_{19}$H$_{20}$ClNO$_3$ m/z 378 (M+Na)$^+$.

EXAMPLE 8

N-(2-{[(6-chloro-4H-1,3-benzodioxin-8-yl)methyl]thio}phenyl)-3-methylbutanamide

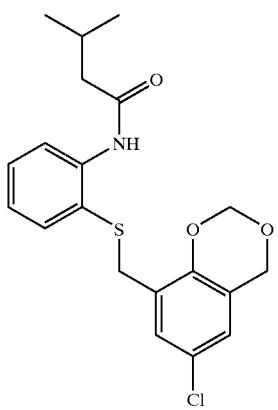

Prepared in the manner of Example 6, step 2, except 3-methylbutanoyl chloride was substituted for 2,2-dimethylpropanoyl chloride. $^1$H NMR (CDCl$_3$) δ 8.41–8.35 (m, 2 H), 7.40 (dd, 1 H), 7.38–7.31 (m, 1 H), 7.02–6.97 (m, 1 H), 6.35–6.32 (m, 2 H), 4.98 (s, 2 H), 4.79 (s, 2 H), 3.84 (s, 2 H), 2.18–2.16 (m, 3 H), 1.02–1.00 (m, 6 H); MS (ESI+) for C$_{20}$H$_{22}$ClNO$_3$S m/z 392 (M+H)$^+$.

EXAMPLE 9

N-(2-{[(7-methoxy-2-oxo-2H-chromen-4-yl)methyl]thio}phenyl)-2,2-dimethylpropanamide Prepared in the manner of Example 4, except 4-(bromomethyl)-7-methoxy-2H-chromen-2-one was substituted for 5-chloro-6-(chloromethyl)-1,3-benzodioxole and 2,2-dimethylpropanoyl chloride was substituted for acetyl chloride. $^1$H NMR (CDCl$_3$) δ 8.60 (s, 1 H), 8.45 (dd, 1 H), 7.45 (d, 1 H), 7.42–7.34 (m, 2 H), 7.04–7.00 (m, 1 H), 6.87–6.83 (m, 2 H), 5.70 (s, 1 H), 3.90 (s, 2 H), 3.88 (s, 3 H), 1.16 (s, 9 H); MS (ESI+) for C$_{22}$H$_{23}$NO$_4$S m/z 398 (M+H)$^+$.

EXAMPLE 10

N-(2-{[(6-chloro-1,3-benzodioxol-5-yl)methyl]thio}phenyl)-2,2-dimethylpropanamide

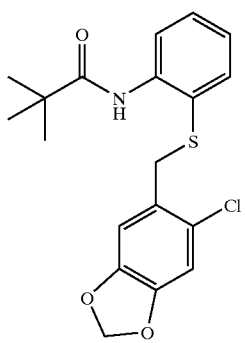

Prepared in the manner of Example 4, except 2,2-dimethylpropanoyl chloride was substituted for acetyl chloride. $^1$H NMR (CDCl$_3$) δ 8.81 (s, 1 H), 8.45 (dd, 1 H), 7.47 (dd, 1 H), 7.36–7.31 (m, 1 H), 7.04–6.99 (m, 1 H), 6.81 (s, 1 H), 6.24 (s, 1 H), 5.92 (s, 2 H), 3.93 (s, 2 H), 1.27 (s, 9 H); MS (ESI+) for C$_{19}$H$_{20}$ClNO$_3$S m/z 378 (M+H)$^+$.

EXAMPLE 11

N-{2-[(2-methoxy-5-nitrobenzyl)thio]phenyl}-2,2-dimethylpropanamide

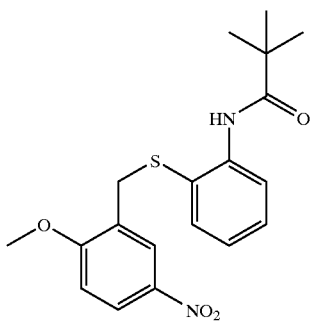

Prepared in the manner of Example 4, except 2-(bromomethyl)-1-methoxy-4-nitrobenzene was substituted for 5-chloro-6-(chloromethyl)-1,3-benzodioxole and 2,2-dimethylpropanoyl chloride was substituted for acetyl chloride. $^1$H NMR (CDCl$_3$) δ 8.79 (s, 1 H), 8.36 (dd, 1 H), 8.05 (dd, 1 H), 7.78 (d, 1 H), 7.28–7.20 (m, 2 H), 6.89–6.85 (m, 1 H), 6.76 (d, 1 H), 3.89 (s, 2 H), 3.68 (s, 3 H), 1.21 (s, 9 H); MS (ESI+) for C$_{19}$H$_{22}$N$_2$O$_4$S m/z 375 (M+H)$^+$.

EXAMPLE 12

3-chloro-N-(2-{[(6-chloro-4H-1,3-benzodioxin-8-yl)methyl]thio}phenyl)-2,2-dimethylpropanamide

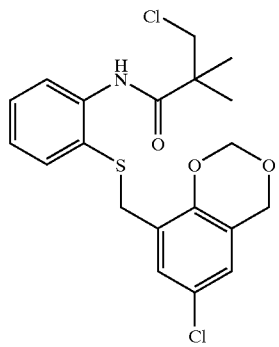

Prepared in the manner of Example 6, step 2, except 3-chloro-2,2-dimethylpropanoyl chloride was substituted for 2,2-dimethylpropanoyl chloride.

$^1$H NMR (CDCl$_3$) δ 8.93 (s, 1 H), 8.45 (dd, 1 H), 7.39 (dd, 1 H), 7.38–7.32 (m, 1 H), 7.03–6.98 (m, 1 H), 6.82 (m, 1 H), 6.78 (m, 1 H), 5.01 (s, 2 H), 4.78 (s, 2 H), 3.86 (s, 2 H), 3.68 (s, 2 H), 1.39 (s, 6 H); MS (ESI+) for C$_{20}$H$_{21}$Cl$_2$NO$_3$S m/z 426 (M+H)$^+$.

EXAMPLE 13

N-(2-{[(6-chloro-4H-1,3-benzodioxin-8-yl)methyl]thio}phenyl)-cyclohexanecarboxamide

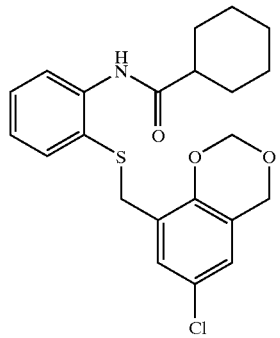

Prepared in the manner of Example 6, step 2, except cyclohexanecarbonyl chloride was substituted for 2,2-dimethylpropanoyl chloride. $^1$H NMR (CDCl$_3$) δ 8.48 (s, 1 H), 8.42 (dd, 1 H), 7.41 (dd, 1 H), 7.35–7.30 (m, 1 H), 7.03–6.97 (m, 1 H), 6.81 (s, 2 H), 4.97 (s, 2 H), 4.78 (s, 2 H), 3.82 (s, 2 H), 2.20–2.10 (m, 1 H), 1.95–1.88 (m, 2 H), 1.88–1.79 (m, 2 H), 1.73–1.68 (m, 1 H), 1.50–1.20 (m, 5 H); MS (ESI+) for C$_{22}$H$_{24}$ClNO$_3$S m/z 418 (M+H)$^+$.

EXAMPLE 14

N-(2-{[(6-chloro-4H-1,3-benzodioxin-8-yl)methyl]thio}phenyl)-cyclopentanecarboxamide

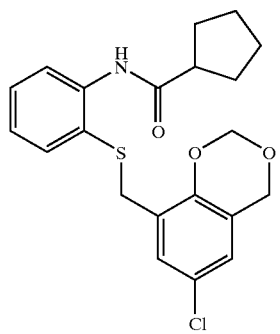

Prepared in the manner of Example 6, step 2, except cyclopentanecarbonyl chloride was substituted for 2,2-dimethylpropanoyl chloride. $^1$H NMR (CDCl$_3$) δ 8.45 (s, 1 H), 8.40 (dd, 1 H), 7.41 (dd, 1 H), 7.35–7.00 (m, 1 H), 7.00–6.95 (m, 1 H), 6.84–6.80 (m, 2 H), 4.97 (s, 2 H), 4.78 (s, 2 H), 3.83 (s, 2 H), 2.67–2.59 (m, 1 H), 1.98–1.58 (m, 8 H); MS (ESI+) for C$_{21}$H$_{22}$ClNO$_3$S m/z 404 (M+H)$^+$.

EXAMPLE 15

N-(2-{[(6-chloro-4H-1,3-benzodioxin-8-yl)methyl]thio}phenyl)-3,3-dimethylbutanamide

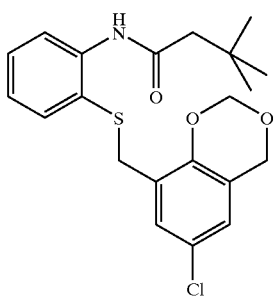

Prepared in the manner of Example 6, step 2, except 3,3-dimethylbutanoyl chloride was substituted for 2,2-dimethylpropanoyl chloride. $^1$H NMR (CDCl$_3$) δ 8.40 (dd, 1 H), 8.31 (s, 1 H), 7.39 (dd, 1 H), 7.35–7.29 (m, 1 H), 7.01–6.96 (m, 1 H), 6.85–6.81 (m, 2 H), 4.99 (s, 2 H), 4.78 (s, 2 H), 3.82 (s, 2 H), 2.15 (s, 2 H), 1.09 (s, 9 H); MS (ESI+) for C$_{21}$H$_{24}$ClNO$_3$S m/z 406 (M+H)$^+$.

EXAMPLE 16

2,2,2-trichloro-N-(2-{[(6-chloro-1,3-benzodioxol-5-yl)methyl]thio}phenyl)-acetamide

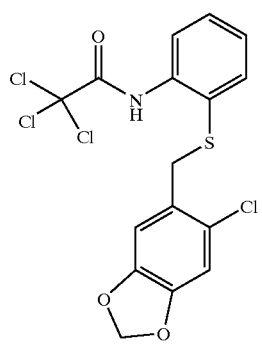

Prepared in the manner of Example 3, except 5-chloro-6-(chloromethyl)-1,3-benzodioxole was substituted for 6-chloro-8-(chloromethyl)-4H-1,3-benzodioxine in step 1 and trichloroacetyl chloride was substituted for 2,2-dimethylpropanoyl chloride in step 2. $^1$H NMR (CDCl$_3$) δ 9.82 (s, 1 H), 8.35 (dd, 1 H), 7.57 (dd, 1 H), 7.45–7.40 (m, 1 H), 7.20–7.13 (m, 1 H), 6.80 (s, 1 H), 6.20 (s, 1 H), 5.92 (s, 2 H), 3.94 (s, 2 H); MS (ESI+) for C$_{16}$H$_{11}$Cl$_4$NO$_3$S m/z 462 (M+Na)$^+$.

EXAMPLE 17

N-(2-{[(6-chloro-1,3-benzodioxol-5-yl)methyl]thio}phenyl)adamantane-1-carboxamide

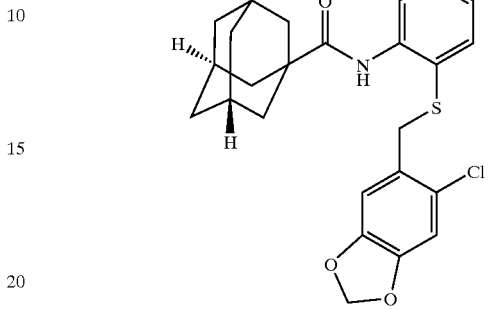

Prepared in the manner of Example 3, except 5-chloro-6-(chloromethyl)-1,3-benzodioxole was substituted for 6-chloro-8-(chloromethyl)-4H-1,3-benzodioxine in step 1 and adamantane-1-carbonyl chloride was substituted for 2,2-dimethylpropanoyl chloride in step 2. $^1$H NMR (CDCl$_3$) δ 8.77 (s, 1 H), 8.47 (dd, 1 H), 7.48 (dd, 1 H), 7.37–7.30 (m, 1 H), 7.04–6.98 (m, 1 H), 6.80 (s, 1 H), 6.22 (s, 1 H), 5.91 (s, 2 H), 3.92 (s, 2 H), 2.10–1.67 (series of m, 15 H); MS (ESI+) for C$_{25}$H$_{26}$ClNO$_3$S m/z 456 (M+H)$^+$.

EXAMPLE 18

N-(2-{[(6-chloro-4H-1,3-benzodioxin-8-yl)methyl]thio}phenyl)adamantane-1-carboxamide

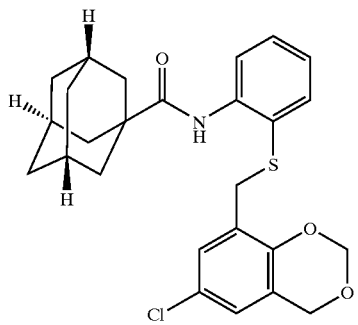

Prepared in the manner of Example 3, except adamantane-1-carbonyl chloride was substituted for 2,2-dimethylpropanoyl chloride in step 2. $^1$H NMR (CDCl$_3$) δ 8.80 (s, 1 H), 8.48 (dd, 1 H), 7.40 (dd, 1 H), 7.36–7.30 (m, 1 H), 7.01–6.96 (m, 1 H), 6.82–6.78 (m, 2 H), 4.97 (s, 2 H), 4.77 (s, 2 H), 3.84 (s, 2 H), 2.12–1.67 (series of m, 15 H); MS (ESI+) for C$_{26}$H$_{28}$ClNO$_3$S m/z 470 (M+H)$^+$.

EXAMPLE 19

N-(2-{[(6-chloro-1,3-benzodioxol-5-yl)methyl]
thio}phenyl)-4,7,7-trimethyl-3-oxo-2-oxabicyclo
[2.2.1]heptane-1-carboxamide

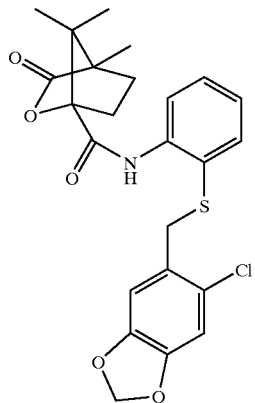

Prepared in the manner of Example 3, except 5-chloro-6-(chloromethyl)-1,3-benzodioxole was substituted for 6-chloro-8-(chloromethyl)-4H-1,3-benzodioxine in step 1 and 4,7,7-trimethyl-3-oxo-2-oxabicyclo[2.2.1]heptane-1-carbonyl chloride was substituted for 2,2-dimethylpropanoyl chloride in step 2. $^1$H NMR (CDCl$_3$) δ 9.45 (s, 1 H), 8.42 (dd, 1 H), 7.45 (dd, 1 H), 7.41–7.34 (m, 1 H), 7.18–7.11 (m, 1 H), 6.80 (s,1 H), 6.54 (s, 1 H), 5.95 (s, 2 H), 3.96 (s, 2 H), 2.65–2.55 (m, 1 H), 2.05–1.95 (m, 2 H), 1.80–1.71 (m, 1 H), 1.16 (s, 6 H), 0.98 (s, 3 H);MS (ESI+) for C$_{24}$H$_{24}$ClNO$_5$S m/z 474 (M+H)$^+$.

EXAMPLE 20

2-[(2-{[(6-chloro-1,3-benzodioxol-5-yl)methyl]
thio}phenyl)amino]-1,1-dimethyl-2-oxoethyl acetate

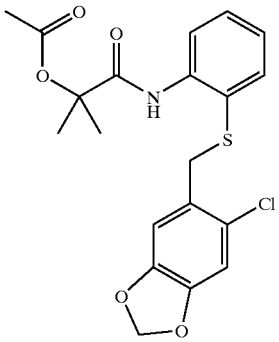

Prepared in the manner of Example 3, except 5-chloro-6-(chloromethyl)-1,3-benzodioxole was substituted for 6-chloro-8-(chloromethyl)-4H-1,3-benzodioxine in step 1 and 4,7,7-trimethyl-3-oxo-2-oxabicyclo[2.2.1]heptane-1-carbonyl chloride was substituted for 2-chloro-1,1-dimethyl-2-oxoethyl acetate in step 2. $^1$H NMR (CDCl$_3$) δ 9.31 (s, 1 H), 8.45 (dd, 1 H), 7.45 (dd, 1 H), 7.40–7.34 (m, 1 H), 7.08–7.02 (m, 1 H), 6.82 (s, 1 H), 6.33 (s, 1 H), 5.95 (s, 2 H), 3.95 (s, 2 H), 2.18 (s, 3 H), 1.71 (s, 6 H); MS (ESI+) for C$_{20}$H$_{20}$ClNO$_5$S m/z 422 (M+H)$^+$.

EXAMPLE 21

N-(2-{[(6-chloro-1,3-benzodioxol-5-yl)methyl]
thio}phenyl)-1-methylcyclohexanecarboxamide

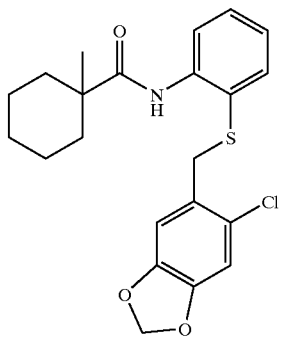

Prepared in the manner of Example 4, except 1-methylcyclohexanecarbonyl chloride was substituted for acetyl chloride. MS (ESI+) for C$_{22}$H$_{24}$ClNO$_3$S m/z 418 (M+H)$^+$.

EXAMPLE 22

N-(2-{[(6-chloro-4H-1,3-benzodioxin-8-yl)methyl]
thio}phenyl)-1-methylcyclohexanecarboxamide

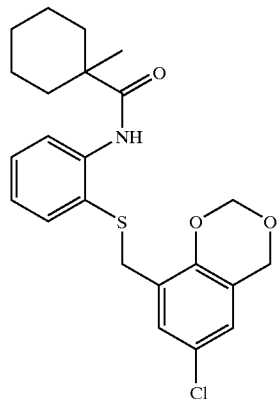

Prepared in the manner of Example 6, step 2, except 1-methylcyclohexane-carbonyl chloride was substituted for 2,2 dimethylpropanoyl chloride. MS (ESI+) for C$_{23}$H$_{26}$ClNO$_3$S m/z 432 (M+H)$^+$.

EXAMPLE 23

N-(2-{[(6-chloro-1,3-benzodioxol-5-yl)methyl]thio}phenyl)-2-hydroxy-2-methylpropanamide

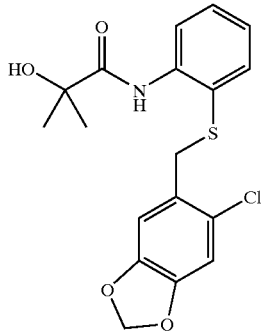

The material from Example 20 was treated with potassium carbonate in methanol overnight. The solvent was evaporated under a stream of nitrogen and the residue chromatographed on silica to give the title product. MS (ESI+) for $C_{18}H_{18}ClNO_4S$ m/z 380 (M+H)+.

EXAMPLE 24

N-(2-{[(6-chloro-1,3-benzodioxol-5-yl)methyl]thio}-5-methylphenyl)-2,2-dimethylpropanamide

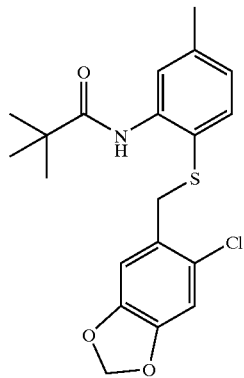

Step 1

5-chloro-6-{[(4-methyl-2-nitrophenyl)thio]methyl}-1,3-benzodioxole 1-bromo-4-methyl-2-nitrobenzene (3 mmol) dissolved in DMF (3 mL) was combined with a solution of sodium sulfide nonahydrate (3 mmol) in water 3 (mL) and stirred for 48 hours. A solution of 5-chloro-6-(chloromethyl)-1,3-benzodioxole (3 mmol) in ethyl acetate (5 mL) was added in and the reaction was agitated for another 24 hours. The reaction was diluted with ethyl acetate and washed sequentially with 0.5 N NaOH solution (7 mL×1), water (7 mL×3) and brine (7 mL×1). The solvent was removed under a stream of nitrogen and the residue crystallized from a mix of dichloromethane and hexane.

Step 2

2-{[(6-chloro-1,3-benzodioxol-5-yl)methyl]thio}-5-methylaniline

The material from step 1 dissolved in ethanol (5 mL) was combined with a solution of tin dichloride dihydrate (12 mmol) in ethanol (5 mL) and heated to 70 for 5 h. The solvent was removed under a stream of nitrogen and the residue was redissolved in a mix of dichloromethane and 1 N NaOH solution. The mixture was applied to an Extrelut QE solid phase extraction column that was prepped with 1 N NaOH solution. The organic was collected and the solvent was removed under a stream of nitrogen. The residue was redissolved in diethyl ether and treated with 4 N HCl in dioxane. The precipate was collected to give the product as the HCl salt.

Step 3

N-(2-{[(6-chloro-1,3-benzodioxol-5-yl)methyl]thio}-5-methylphenyl)-2,2-dimethylpropanamide The material from step 2 was suspended in a mixture of diisopropyl ethyl amine (0.15 mL), PS-DMAP resin (50 mg), 2,2-dimethylpropanoyl chloride (0.1 mL) and dichloromethane (7 mL). The reaction was agitated overnight and then treated with PS-Trisamine resin and agitated a further 24 h. The reaction was applied to an Extrelut QE column prepped with 1N HCl, the organic was collected and evaporated under a stream of nitrogen. The residue was chromatographed on silica to afford the title product. MS (ESI+) for $C_{20}H_{22}ClNO_3S$ m/z 392 (M+H)+.

EXAMPLE 25

N-(2-{[(6-chloro-1,3-benzodioxol-5-yl)methyl]thio}-3-methylphenyl)-2,2-dimethylpropanamide

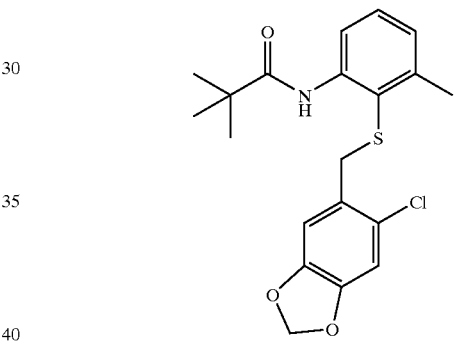

Prepared in the manner of Example 24, except 2-chloro-1-methyl-3-nitrobenzene was substituted for 1-bromo-4-methyl-2-nitrobenzene in step 1. MS (ESI+) for $C_{20}H_{22}ClNO_3S$ m/z 392 (M+H)+.

EXAMPLE 26

N-(3-chloro-2-{[(6-chloro-1,3-benzodioxol-5-yl)methyl]thio}phenyl)-2,2-dimethylpropanamide

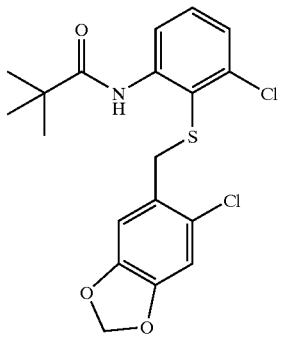

Prepared in the manner of Example 24, except 1,2-dichloro-3-nitrobenzene was substituted for 1-bromo-4-methyl-2-nitrobenzene in step 1. MS (ESI+) for $C_{19}H_{19}Cl_2NO_3S$ m/z 412 (M+H)$^+$.

EXAMPLE 27

N-(5-chloro-2-{[(6-chloro-1,3-benzodioxol-5-yl)methyl]thio}phenyl)-2,2-dimethylpropanamide

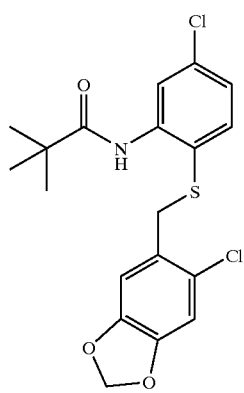

Prepared in the manner of Example 24, except 1,4-dichloro-2-nitrobenzene was substituted for 1-bromo-4-methyl-2-nitrobenzene in step 1. MS (ESI+) for $C_{19}H_{19}Cl_2NO_3S$ m/z 412 (M+H)$^+$.

EXAMPLE 28

N-(2-{[(6-chloro-1,3-benzodioxol-5-yl)methyl]thio}-5-fluorophenyl)-2,2-dimethylpropanamide

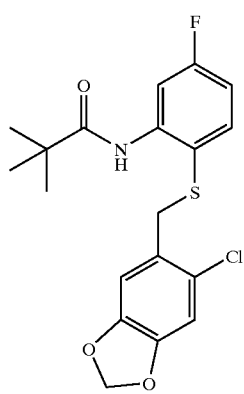

Prepared in the manner of Example 24, except 1,4-difluoro-2-nitrobenzene was substituted for 1-bromo-4-methyl-2-nitrobenzene in step 1. MS (ESI+) for $C_{19}H_{19}ClFNO_3S$ m/z 396 (M+H)$^+$.

EXAMPLE 29

N-(2-{[(6-chloro-1,3-benzodioxol-5-yl)methyl]thio}-4,5-difluorophenyl)-2,2-dimethylpropanamide

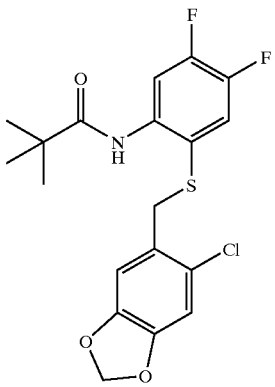

Prepared in the manner of Example 24, except 1,2,4-trifluoro-5-nitrobenzene was substituted for 1-bromo-4-methyl-2-nitrobenzene in step 1. MS (ESI+) for $C_{19}H_{18}ClF_2NO_3S$ m/z 414 (M+H)$^+$.

EXAMPLES 30–47

2-amino thiophenol (20 mmol) was dissolved in dichloromethane (65 mL). The appropriate alkyl halide (20 mmol) was added along with PS-DIEA resin (8.00 g, 3.83 mmol/g, 30.64 mmol) and the mixture was agitated at room temperature overnight. The product was isolated as a stock solution in dichloromethane. This product was then acylated by using excess of the appropriate acid chloride, PS-DMAP resin, PS-DIEA in dichloromethane and agitating the reaction overnight at room temperature. PS-Trisamine was added in and the reaction agitated a further 18 h. The reaction was filtered and the filtrate was reduced under a stream of nitrogen to afford the product.

| Example Number | Structure | Compound Name(s) | Mass Spec |
|---|---|---|---|
| 30 | 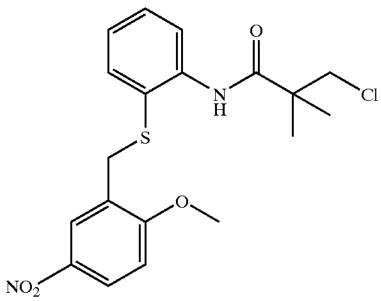 | 3-chloro-N-{2-[(2-methoxy-5-nitrobenzyl)thio]phenyl}-2,2-dimethylpropanamide | 409.2 |
| 31 | 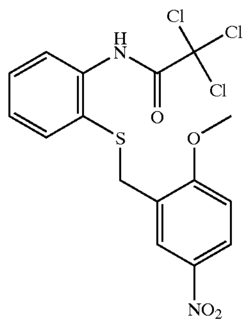 | 2,2,2-trichloro-N-{2-[(2-methoxy-5-nitrobenzyl)thio]phenyl}acetamide | 435.0 |
| 32 | 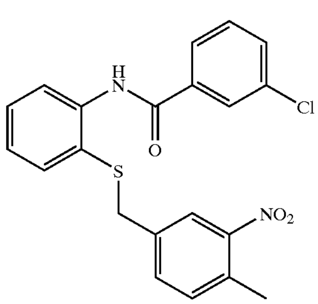 | 3-chloro-N-{2-[(4-methyl-3-nitrobenzyl)thio]phenyl}benzamide | 413.0 |
| 33 | 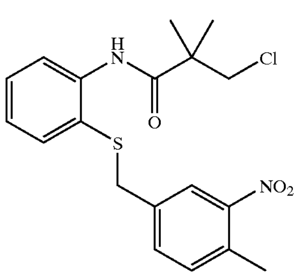 | 3-chloro-2,2-dimethyl-N-{2-[(4-methyl-3-nitrobenzyl)thio]phenyl}propanamide | 393.0 |
| 34 | 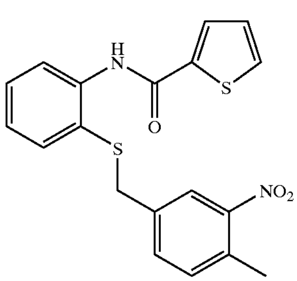 | N-{2-[(4-methyl-3-nitro benzyl)thio]phenyl}thiophene-2-carboxamide | 385.0 |

-continued

| Example Number | Structure | Compound Name(s) | Mass Spec |
|---|---|---|---|
| 35 | 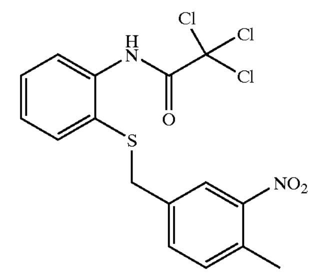 | 2,2,2-trichloro-N-{2-[(4-methyl-3-nitrobenzyl)thio]phenyl}acetamide | 419.0 |
| 36 | 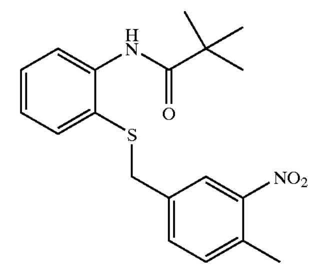 | 2,2-dimethyl-N-{2-[(4-methyl-3-nitrobenzyl)thio]phenyl}propanamide | 359.2 |
| 37 | 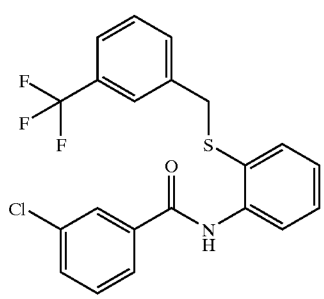 | 3-chloro-N-(2-{[3-(trifluoromethyl)benzyl]thio}phenyl)benzamide | 422.0 |
| 38 | 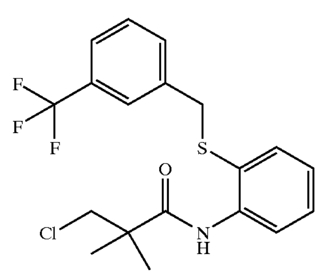 | 3-chloro-2,2-dimethyl-N-(2-{[3-(trifluoromethyl)benzyl]thio}phenyl)propanamide | 402.0 |
| 39 | 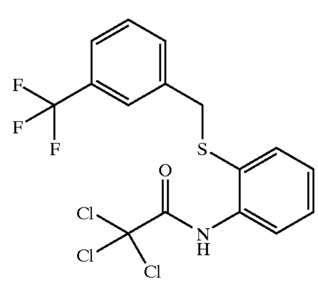 | 2,2,2-trichloro-N-(2-{[3-(trifluoromethyl)benzyl]thio}phenyl)acetamide | 430.0 |

-continued

| Example Number | Structure | Compound Name(s) | Mass Spec |
|---|---|---|---|
| 40 | 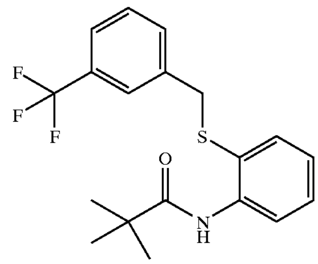 | 2,2-dimethyl-N-(2-{[3-(trifluoro methyl)benzyl]thio}phenyl) propanamide | 368.0 |
| 41 | 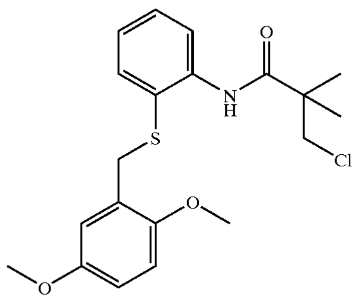 | 3-chloro-N-{2-[(2,5-di methoxybenzyl)thio]phenyl}-2,2-dimethylpropanamide | 394.2 |
| 42 | 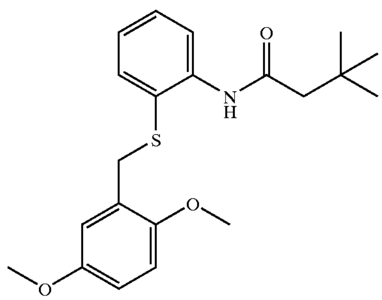 | N-{2-[(2,5-dimethoxy benzyl)thio]phenyl}-3,3-dimethylbutanamide | 374.2 |
| 43 | 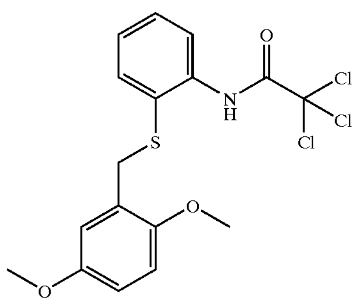 | 2,2,2-trichloro-N-{2-[(2,5-di methoxybenzyl)thiol] phenyl}acetamide | 440.0 (M + 23) |
| 44 | 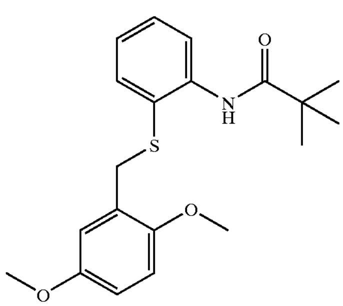 | N-{2-[(2,5-dimethoxy benzyl)thio] phenyl}-2,2-dimethylpropanamide | 360.2 |

-continued

| Example Number | Structure | Compound Name(s) | Mass Spec |
|---|---|---|---|
| 45 | 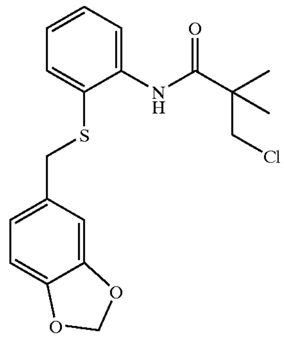 | N-{2-[(1,3-benzodioxol-5-ylmethyl)thio]phenyl}-3-chloro-2,2-dimethylpropanamide | 378.0 |
| 46 | 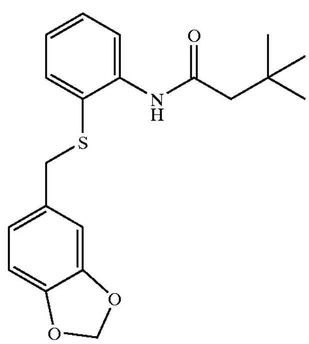 | N-{2-[(1,3-benzodioxol-5-ylmethyl)thio]phenyl}-3,3-dimethylbutanamide | 358.2 |
| 47 | 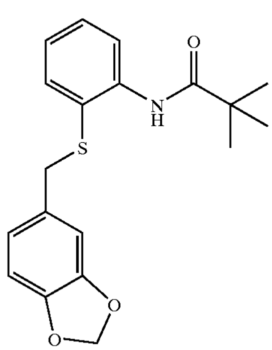 | N-{2-[(1,3-benzodioxol-5-ylmethyl)thio]phenyl}-2,2-dimethylpropanamide | 344.2 |

EXAMPLES 48–52

Prepared in the manner of Example 25, using the appropriate alkyl halide instead of 5-chloro-6-(chloromethyl)-1,3-benzodioxole in step 1 and using the appropriate acyl chloride instead of 2,2-dimethylpropanoyl chloride in step 3.

| Example Number | Structure | Compound Name(s) | Mass Spec |
|---|---|---|---|
| 48 | 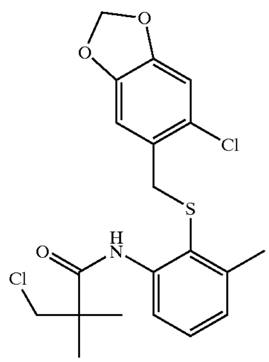 | 3-chloro-N-(2-{[(6-chloro-1,3-benzo dioxol-5-yl)methyl]thio}-3-methyl phenyl)-2,2-dimethylpropanamide | 426.0 |
| 49 | 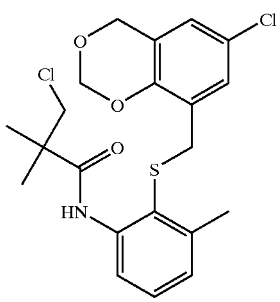 | 3-chloro-N-(2-{[(6-chloro-4H-1,3-benzodioxin-8-yl)methyl]thio}-3-methyl phenyl)-2,2-dimethylpropanamide | 440.0 |
| 50 | 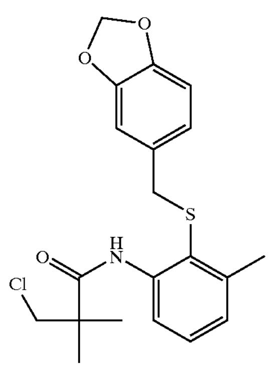 | N-{2-[(1,3-benzodioxol-5-ylmethyl)thio]-3-methylphenyl}-3-chloro-2,2-dimethylpropanamide | 392.2 |
| 51 | 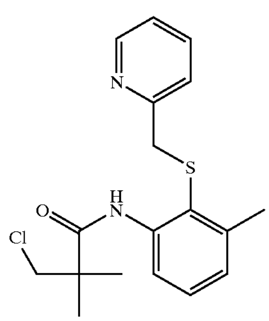 | 3-chloro-2,2-dimethyl-N-{3-methyl-2-[(pyridin-2-ylmethyl)thio]phenyl}propanamide | 349.2 |

-continued

| Example Number | Structure | Compound Name(s) | Mass Spec |
|---|---|---|---|
| 52 | 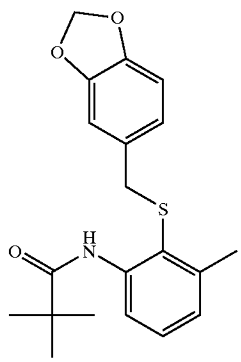 | N-{2-[(1,3-benzodioxol-5-ylmethyl)thio]-3-methylphenyl}-2,2-dimethyl propanamide | 358.2 |

EXAMPLE 53

N-{2-[(5-amino-2-methoxybenzyl)thio]phenyl}-2,2-dimethylpropanamide hydrochloride

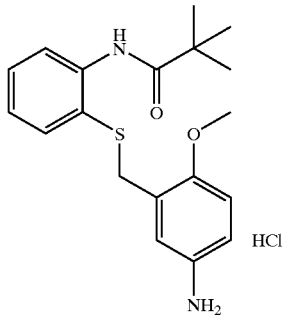

The product of Example 11 dissolved in ethanol and treated with 4 equivalents of Tin(II) dichloride dihydrate at reflux for 4 h. The reaction was cooled, diluted with water, made basic with potassium hydroxide and extracted with ethyl acetate (3×250 mL). The combined organics were washed with water then saturated sodium chloride solution. The solvent was removed in vacuo and the residue dissolved in diethyl ether. 4 N HCl in dioxane was added in excess and the resulting precipitate was filtered by suction to afford the product. 345.2 M+1

EXAMPLES 54–57

The product of Example 53 was combined with an excess of the appropriate aldehyde or ketone in methanol. A solution of sodium cyanoborohydride in methanol was added in and the pH was corrected to 5 with acetic acid. The reaction was agitated for 4 d then PS-TsNHNH2 resin was added and the reaction agitated a further 3 hours. The reactions were filtered and the filtrate was dried to a residue which was chromatographed on silica to afford the product.

| Example Number | Structure | Compound Name(s) | Mass Spec |
|---|---|---|---|
| 54 | 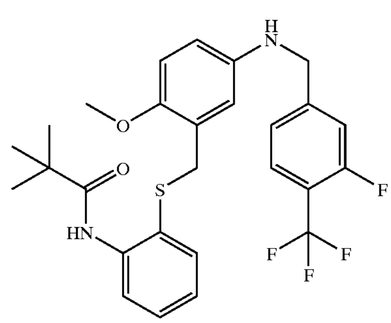 | N-{2-[(5-{[3-fluoro-4-(trifluoromethyl)benzyl]amino}-2-methoxybenzyl)thio]phenyl}-2,2-dimethyl propanamide | 521.2 |

-continued

| Example Number | Structure | Compound Name(s) | Mass Spec |
|---|---|---|---|
| 55 | 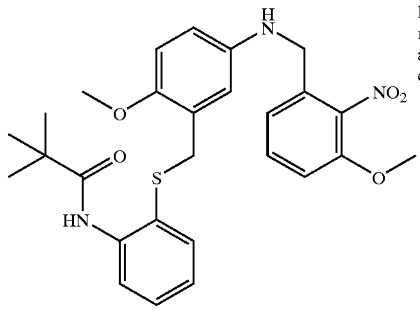 | N-[2-({2-methoxy-5-[(3-methoxy-2-nitrobenzyl)amino]benzyl}thio)phenyl]-2,2-dimethyl propanamide | 510.2 |
| 56 | 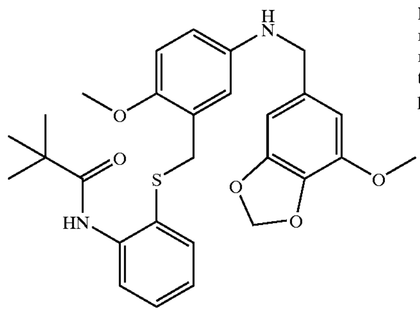 | N-{2-[(2-methoxy-5-{[(7-methoxy-1,3-benzodioxol-5-yl)methyl]amino}benzyl)thio]phenyl}-2,2-dimethyl propanamide | 509.2 |
| 57 | 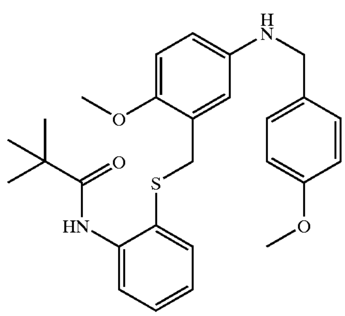 | N-[2-({2-methoxy-5-[(4-methoxybenzyl)amino]benzyl}thio)phenyl]-2,2-dimethylpropanamide | 465.2 |

EXAMPLES 58–60

The product of Example 53 was acylated by using excess of the appropriate acid chloride, PS-DMAP resin, PS-DIEA in dichloromethane and agitating the reaction overnight at room temperature. PS-Trisamine was added in and the reaction agitated a further 18 h. The reaction was filtered and the filtrate was reduced under a stream of nitrogen to afford the product.

| Example No | Structure | Compound Name(s) | Mass Spec |
|---|---|---|---|
| 58 | 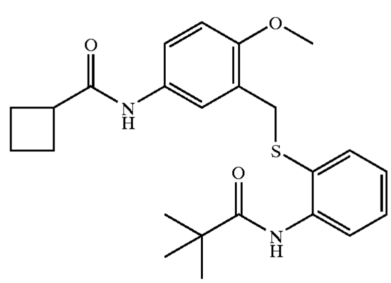 | N-{3-[({2-[(2,2-dimethyl propanoyl)amino]phenyl}thio)methyl]-4-methoxyphenyl}cyclobutanecarboxamide | 427.2 |

-continued

| Example No | Structure | Compound Name(s) | Mass Spec |
|---|---|---|---|
| 59 | 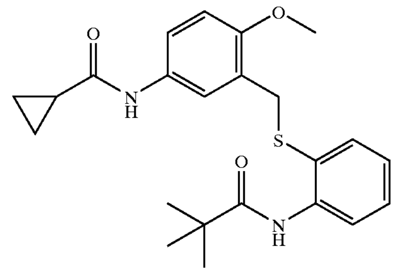 | N-{3-[({2-[(2,2-dimethyl propanoyl)amino]phenyl}thio) methyl]-4-methoxyphenyl}cyclo propanecarboxamide | 413.2 |
| 60 | 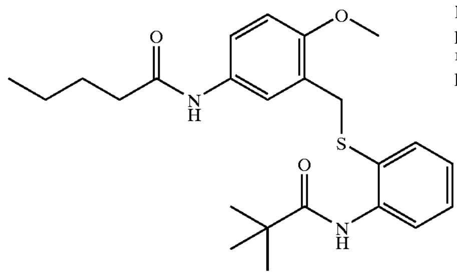 | N-{3-[({2-[(2,2-dimethyl propanoyl)amino]phenyl}thio) methyl]-4-methoxyphenyl} pentanamide | 429.2 |

EXAMPLE 61

LXR Reporter Gene Transactivation Assay for High-Throughput Screen

Human hepatic cells (Huh-7) were cotransfected with a luciferase reporter gene (pGal4-RE), where transcription of luciferase gene is driven by the Gal4 response element, and a chimeric gene construct of liver X receptor (Gal4$_{DBD}$-LXRα$_{LBD}$), which comprises a DNA sequence that encodes a hybrid protein of LXR ligand binding domain (LXR$_{LBD}$) and Gal4 DNA-binding domain (Gal4$_{DBD}$). The transfection was performed in culture dishes using LipofectAMINE2000 reagent. The transfected cells were harvested 20 hr later and resuspended in assay medium containing RPMI 1640 medium, 2% fetal bovine lipoprotein deficient serum, 100 units/ml pencillin and 100 µg/ml streptomycin.

In screening for LXR modulators, the transfected cells were dispensed in an assay plate (384-well white tissue culture plate) containing the test compounds at 10 µM final concentration and incubated for 24 hr. The effects of test compounds on the activation of LXR$_{LBD}$ and hence luciferase transcription was determined by measuring the luciferase activity using Steady-Glo luciferase assay substrate. Luciferase activity results are expressed as the fold-induction relative to DMSO controls. Compounds that exhibited >10 fold induction were then retested and the EC$_{50}$ was determined as the concentration necessary to produce 50% of the maximal luciferase activity. Each of the compounds of Examples 1–60 was found to have an EC$_{50}$ of less than 50 µM.

What is claimed is:

1. A compound corresponding to the formula:

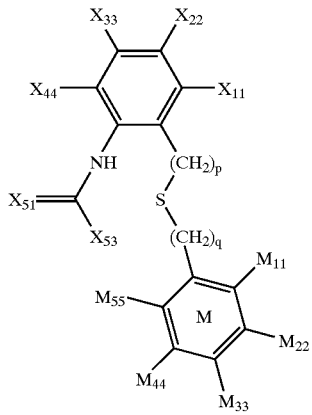

wherein:

$M_{11}$, $M_{22}$, $M_{33}$, $M_{44}$, and $M_{55}$ are independently hydrogen, hydrocarbyl, substituted hydrocarbyl, hydroxy, hydrocarbyloxy, substituted hydrocarbyloxy, mercapto, halo, heterocyclo, nitro, amino, acylamino, acylthio, or acyloxy, provided an adjacent two of $M_{11}$, $M_{22}$, $M_{33}$, $M_{44}$, and $M_{55}$ form a fused ring with the atoms of the M ring to which they are bonded;

p is 0 and q is 1 or 2;

$X_{11}$, $X_{22}$, $X_{33}$, and $X_{44}$, are independently hydrogen, hydrocarbyl, substituted hydrocarbyl, hydroxy, hydrocarbyloxy, substituted hydrocarbyloxy, mercapto, halo, heterocyclo, nitro, amino, acylamino, acylthio, acyloxy, or acyl;

$X_{51}$ is oxygen or sulfur; and $X_{53}$ is hydrogen, hydrocarbyl, substituted hydrocarbyl, heterocyclo, or amino.

2. The compound of claim 1 wherein q is 1.

3. The compound of claim 1 wherein $X_{51}$ is oxygen.

4. The compound of claim 1 wherein $X_{53}$ is heterocyclo, optionally substituted alkyl, or optionally substituted phenyl.

5. The compound of claim 1 wherein one of $X_{11}$, $X_{22}$, $X_{33}$, $X_{44}$ is alkyl, nitro, or halo, and the remainder of $X_{11}$, $X_{22}$, $X_{33}$, and $X_{44}$ are hydrogen.

6. The compound of claim 1 wherein one of $M_{11}$ and $M_{22}$, $M_{22}$ and $M_{33}$, $M_{33}$ and $M_{44}$, or $M_{44}$ and $M_{55}$, and the atoms to which they are attached form a fused ring comprising —O—CH$_2$—O—CH$_2$— or —OCH$_2$O—, and the remainder of $M_{11}$, $M_{22}$, $M_{33}$, $M_{44}$ and $M_{55}$ are hydrogen, halogen, or nitro.

7. The compound of claim 1 wherein one of $M_{11}$ and $M_{22}$, $M_{22}$ and $M_{33}$, $M_{33}$ and $M_{44}$, or $M_{44}$ and $M_{55}$, and the atoms to which they are attached form a fused ring and the remainder of $M_{11}$, $M_{22}$, $M_{33}$, $M_{44}$ and $M_{55}$ are hydrogen.

8. A compound corresponding to the formula:

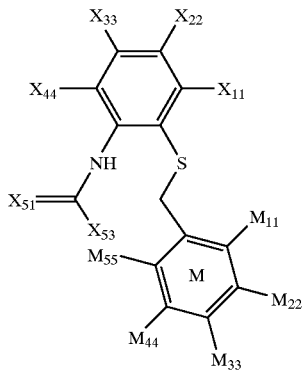

wherein:

$M_{11}$, $M_{22}$, $M_{33}$, $M_{44}$, and $M_{55}$ are independently hydrogen, hydrocarbyl, substituted hydrocarbyl, hydroxy, hydrocarbyloxy, substituted hydrocarbyloxy, mercapto, halo, heterocyclo, nitro, amino, acylamino, acylthio, or acyloxy, provided an adjacent two of $M_{11}$, $M_{22}$, $M_{33}$, $M_{44}$, and $M_{55}$ form a fused ring with the atoms to which they are bonded;

$X_{11}$, $X_{22}$, $X_{33}$, and $X_{44}$, are independently hydrogen, hydrocarbyl, substituted hydrocarbyl, hydroxy, hydrocarbyloxy, substituted hydrocarbyloxy, mercapto, halo, heterocyclo, nitro, amino, acylamino, acylthio, acyloxy or acyl;

$X_{51}$ is oxygen or sulfur; and $X_{53}$ is hydrogen, hydrocarbyl, substituted hydrocarbyl, heterocyclo, or amino.

9. The compound of claim 8 wherein $X_{51}$ is oxygen.

10. The compound of claim 8 wherein $X_{53}$ is heterocyclo, optionally substituted linear, branched or cyclo-alkyl, or optionally substituted phenyl.

11. The compound of claim 8 wherein one of $X_{11}$, $X_{22}$, $X_{33}$, $X_{44}$ is alkyl, nitro, or halo and the others of $X_{11}$, $X_{22}$, $X_{33}$, $X_{44}$ are hydrogen.

12. The compound of claim 8 wherein $M_{11}$ and $M_{22}$, $M_{22}$ and $M_{33}$, $M_{33}$ and $M_{44}$, or $M_{44}$ and $M_{55}$, and the atoms to which they are attached form a fused ring comprising —O—CH$_2$—O—CH$_2$— or —OCH$_2$O—, and the others of $M_{11}$, $M_{22}$, $M_{33}$, $M_{44}$ and $M_{55}$ are hydrogen, halogen, or nitro.

13. The compound of claim 8 wherein one of $M_{11}$ and $M_{22}$, $M_{22}$ and $M_{33}$, $M_{33}$ and $M_{44}$, or $M_{44}$ and $M_{55}$, and the atoms to which they are attached form a fused ring and the remainder of $M_{11}$, $M_{22}$, $M_{33}$, $M_{44}$ and $M_{55}$ are hydrogen.

14. A compound corresponding to the formula:

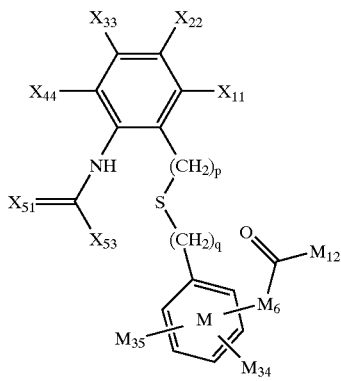

wherein:

$M_6$ is hydrocarbyl, substituted hydrocarbyl, oxygen or amino;

$M_{12}$ is hydrocarbyl, substituted hydrocarbyl, hydroxy, hydrocarbyloxy, substituted hydrocarbyloxy, hydrocarbylthio, substituted hydrocarbylthio or amino;

$M_{34}$ and $M_{35}$ are attached to adjacent atoms and form a fused ring with the atoms of the M ring to which they are bonded;

p is 0 and q is 1 or 2;

$X_{11}$, $X_{22}$, $X_{33}$, and $X_{44}$, are independently hydrogen, hydrocarbyl, substituted hydrocarbyl, hydroxy, hydrocarbyloxy, substituted hydrocarbyloxy, mercapto, halo, heterocyclo, nitro, amino, acylamino, acylthio, acyloxy, or acyl;

$X_{51}$ is oxygen or sulfur; and $X_{53}$ is hydrogen, hydrocarbyl, substituted hydrocarbyl, heterocyclo, or amino.

15. The compound of claim 14 wherein q is 1.

16. The compound of claim 14 wherein $X_{51}$ is oxygen.

17. The compound of claim 14 wherein $X_{53}$ is heterocyclo, optionally substituted alkyl, or optionally substituted phenyl.

18. The compound of claim 14 wherein one of $X_{11}$, $X_{22}$, $X_{33}$, $X_{44}$ is alkyl, nitro, or halo and the others of $X_{11}$, $X_{22}$, $X_{33}$, $X_{44}$ are hydrogen.

19. The compound of claim 14 wherein $M_6$ is —NH—.

20. The compound of claim 14 wherein $M_6$ is —O—.

21. The compound of claim 14 wherein $M_{12}$ is optionally substituted hydrocarbyl.

22. The compound of claim 14 wherein $M_{12}$ is hydroxy or optionally substituted hydrocarbyloxy.

23. The compound of claim 14 wherein $M_{12}$ is amino.

24. A compound corresponding to Formula V:

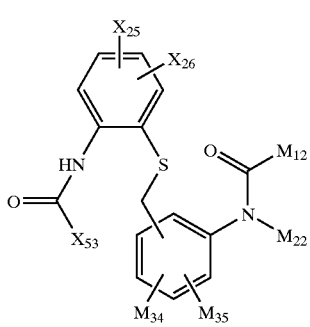

(V)

wherein $X_{25}$ and $X_{26}$ are independently hydrogen, optionally substituted alkyl, nitro or halo, $M_{12}$ is alkoxy, alkylthio, amino, hydrocarbyl or substituted hydrocarbyl;

$M_{22}$ is hydrogen, hydrocarbyl or substituted hydrocarbyl;

$M_{34}$ and $M_{35}$ are attached to adjacent carbon atoms and, in combination with these adjacent carbon atoms define a fused ring; and $X_{53}$ is hydrocarbyl, substituted hydrocarbyl or heterocyclo.

25. The compound of claim 24 wherein $X_{53}$ is heterocyclo.

26. The compound of claim 24 wherein $X_{53}$ is optionally substituted linear, branched or cycloalkyl.

27. The compound of claim 24 wherein one of $X_{25}$ and $X_{26}$ is hydrogen and the other is optionally substituted alkyl, nitro, or halo.

28. The compound of claim 24 wherein $M_{34}$ and $M_{35}$, in combination, are $-O-CH_2-O-CH_2-$ or $-OCH_2O-$.

29. The compound of claim 24 wherein $M_{12}$ is optionally substituted hydrocarbyl.

30. The compound of claim 24 wherein $M_{12}$ is hydroxy or optionally substituted hydrocarbyloxy.

31. The compound of claim 24 wherein $M_{12}$ is amino.

32. The compound of claim 24 wherein $M_{12}$ is hydrocarbyl or substituted hydrocarbyl.

33. The compound of claim 24 wherein $M_{12}$ is alkyl.

34. The compound of claim 24 wherein $M_{22}$ is hydrogen.

35. A compound corresponding to Formula VI:

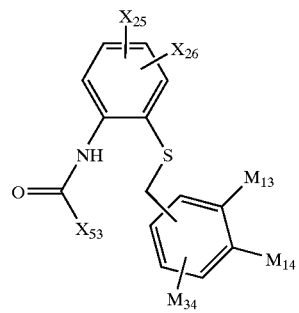

(VI)

wherein $M_{13}$ and $M_{14}$ and the carbon atoms to which they are attached form a five or six-membered fused ring, the ring comprising, in addition to the carbon atoms to which $M_{13}$ and $M_{14}$ are attached, $-O-CH_2-O-CH_2-$ when the ring is a six membered ring, or $-O-CH_2-O-$ when the ring is a five membered ring;

$X_{25}$ and $X_{26}$ are independently hydrogen, optionally substituted alkyl, nitro, or halo;

$M_{34}$ is hydrogen, optionally substituted alkyl, halogen, amino or nitro; and $X_{53}$ is heterocyclo or optionally substituted hydrocarbyl.

36. The compound of claim 35 wherein one of $X_{25}$ and $X_{26}$ is hydrogen.

37. The compound of claim 35 wherein $M_{34}$ is hydrogen.

38. The compound of claim 35 wherein $M_{34}$ is optionally substituted alkyl.

39. The compound of claim 35 wherein $M_{34}$ is amino.

40. The compound of claim 35 wherein $M_{34}$ is nitro.

41. The compound of claim 35 wherein $X_{53}$ is heterocyclo or optionally substituted hydrocarbyl.

42. A compound corresponding to the formula:

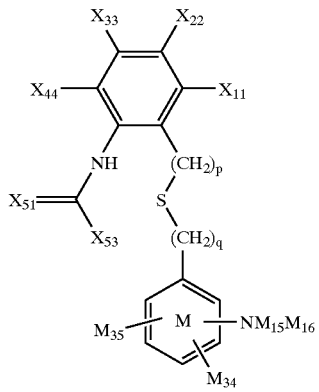

wherein:

$M_{15}$ and $M_{16}$ are independently hydrogen, hydrocarbyl, substituted hydrocarbyl, acyl, or heterocyclo, provided $M_{16}$ and $M_{15}$ are not each acyl;

$M_{34}$ and $M_{35}$ are bonded to adjacent atoms and form a fused ring with the atoms of the M ring to which they are bonded;

p is 0 and q is 1 or 2;

$X_{11}$, $X_{22}$, $X_{33}$, and $X_{44}$, are independently hydrogen, hydrocarbyl, substituted hydrocarbyl, hydroxy, hydrocarbyloxy, substituted hydrocarbyloxy, mercapto, halo, heterocyclo, cyano, nitro, amino, acylamino, acylthio, acyloxy, or acyl;

$X_{51}$ is oxygen or sulfur; and $X_{53}$ is hydrogen, hydrocarbyl, substituted hydrocarbyl, heterocyclo, or amino.

43. The compound of claim 42 wherein q is 1.

44. The compound of claim 42 wherein $X_{51}$ is oxygen.

45. The compound of claim 42 wherein $X_{53}$ is heterocyclo, optionally substituted alkyl, or optionally substituted phenyl.

46. The compound of claim 42 wherein one of $X_{11}$, $X_{22}$, $X_{33}$, $X_{44}$ is alkyl, nitro, or halo and the others of $X_{11}$, $X_{22}$, $X_{33}$, $X_{44}$ are hydrogen.

47. The compound of claim 42 wherein $M_{15}$ is hydrogen and $M_{16}$ is $-C(=O)M_{17}$ wherein $M_{17}$ is hydrocarbyl, substituted hydrocarbyl, hydrocarbyloxy, substituted hydrocarbyloxy, or heterocyclo.

48. A compound corresponding to Formula VIII:

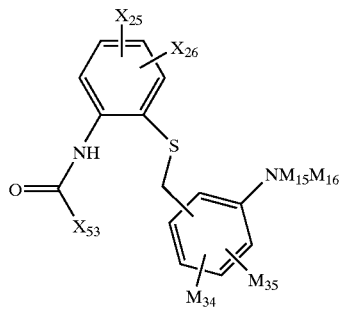

(VIII)

wherein:

M$_{15}$ and M$_{16}$ are independently hydrogen, hydrocarbyl, substituted hydrocarbyl, or acyl, provided M$_{15}$ and M$_{16}$ are not each acyl;

M$_{34}$ and M$_{35}$ are bonded to adjacent carbon atoms and, in combination, form a fused ring with the carbon atoms to which they are bonded;

X$_{25}$ and X$_{26}$ are independently hydrogen, optionally substituted alkyl, nitro, or halo; and X$_{53}$ is heterocyclo, optionally substituted alkyl, or optionally substituted phenyl.

49. A compound of claim 48 wherein one of X$_{25}$ and X$_{26}$ is hydrogen.

50. The compound of claim 48 wherein X$_{53}$ is optionally substituted linear, branched or cyclo-alkyl.

51. The compound of claim 48 wherein X$_{53}$ is heterocyclo.

52. The compound of claim 48 wherein one of X$_{25}$ and X$_{26}$ is hydrogen and the other is optionally substituted alkyl, nitro, or halo.

53. The compound of claim 48 wherein M$_{34}$ and M$_{35}$ are, in combination —O—CH$_2$—O—CH$_2$— or —OCH$_2$O—.

54. The compound of claim 48 wherein M$_{15}$ is hydrogen and M$_{16}$ is acyl.

55. The compound of claim 48 wherein M$_{15}$ is hydrogen and M$_{16}$ is hydrocarbyl or substituted hydrocarbyl.

56. A compound selected from the group consisting of

N-(2-{[(6-chloro-1,3-benzodioxol-5-yl)methyl]thio}phenyl)thiophene-2-carboxamide;

N-(2-{[(6-chloro-1,3-benzodioxol-5-yl)methyl]thio}phenyl)acetamide;

N-(2-{[(6-chloro-1,3-benzodioxol-5-yl)methyl]thio}phenyl)-2,2,2-trifluoroacetamide;

N-(2-{[(6-chloro-4H-1,3-benzodioxin-8-yl)methyl]thio}phenyl)-2,2-dimethylpropanamide;

N-(2-{[(6-chloro-4H-1,3-benzodioxin-8-yl)methyl]thio}phenyl)-2-methylpropanamide;

N-(2-{[(6-chloro-4H-1,3-benzodioxin-8-yl)methyl]thio}phenyl)-3-methylbutanamide;

N-(2-{[(6-chloro-1,3-benzodioxol-5-yl)methyl]thio}phenyl)-2,2-dimethylpropanamide;

3-chloro-N-(2-{[(6-chloro-4H-1,3-benzodioxin-8-yl)methyl]thio}phenyl)-2,2-dimethylpropanamide;

N-(2-{[(6-chloro-4H-1,3-benzodioxin-8-yl)methyl]thio}phenyl)-cyclohexanecarboxamide;

N-(2-{[(6-chloro-4H-1,3-benzodioxin-8-yl)methyl]thio}phenyl)-cyclopentanecarboxamide;

N-(2-{[(6-chloro-4H-1,3-benzodioxin-8-yl)methyl]thio}phenyl)-3,3-dimethylbutanamide;

2,2,2-trichloro-N-(2-{[(6-chloro-1,3-benzodioxol-5-yl)methyl]thio}phenyl)-acetamide;

N-(2-{[(6-chloro-1,3-benzodioxol-5-yl)methyl]thio}phenyl)adamantane-1-carboxamide;

N-(2-{[(6-chloro-4H-1,3-benzodioxin-8-yl)methyl]thio}phenyl)adamantane-1-carboxamide;

N-(2-{[(6-chloro-1,3-benzodioxol-5-yl)methyl]thio}phenyl)-4,7,7-trimethyl-3-oxo-2-oxabicyclo[2.2.1]heptane-1-carboxamide;

2-[(2-{[(6-chloro-1,3-benzodioxol-5-yl)methyl]thio}phenyl)amino]-1,1 dimethyl-2-oxoethyl acetate;

N-(2-{[(6-chloro-1,3-benzodioxol-5-yl)methyl]thio}phenyl)-1-methyl cyclohexanecarboxamide;

N-(2-{[(6-chloro-4H-1,3-benzodioxin-8-yl)methyl]thio}phenyl)-1-methylcyclohexanecarboxamide;

N-(2-{[(6-chloro-1,3-benzodioxol-5-yl)methyl]thio}phenyl)-2-hydroxy-2-methylpropanamide;

N-(2-{[(6-chloro-1,3-benzodioxol-5-yl)methyl]thio}-5-methylphenyl)-2,2-dimethylpropanamide;

N-(2-{[(6-chloro-1,3-benzodioxol-5-yl)methyl]thio}-3-methylphenyl)-2,2-dimethylpropanamide;

N-(3-chloro-2-{[(6-chloro-1,3-benzodioxol-5-yl)methyl]thio}phenyl)-2,2-dimethylpropanamide;

N-(5-chloro-2-{[(6-chloro-1,3-benzodioxol-5-yl)methyl]thio}phenyl)-2,2-dimethylpropanamide;

N-(2-{[(6-chloro-1,3-benzodioxol-5-yl)methyl]thio}-5-fluorophenyl)-2,2-dimethylpropanamide;

N-(2-{[(6-chloro-1,3-benzodioxol-5-yl)methyl]thio}-4,5-difluorophenyl)-2,2-dimethylpropanamide;

N-{2-[(1,3-benzodioxol-5-ylmethyl)thio]phenyl}-3-chloro-2,2-dimethyl propanamide;

N-{2-[(1,3-benzodioxol-5-ylmethyl)thio]phenyl}-3,3-dimethyl butanamide;

N-{2-[(1,3-benzodioxol-5-ylmethyl)thio]phenyl}-2,2-dimethyl propanamide;

3-chloro-N-(2-{[(6-chloro-1,3-benzodioxol-5-yl)methyl]thio}-3-methylphenyl)-2,2-dimethylpropanamide;

3-chloro-N-(2-{[(6-chloro-4H-1,3-benzodioxin-8-yl)methyl]thio}-3-methylphenyl)-2,2-dimethylpropanamide;

N-{2-[(1,3-benzodioxol-5-ylmethyl)thio]-3-methylphenyl}-3-chloro-2,2-dimethyl propanamide; and N-{2-[(1,3-benzodioxol-5-ylmethyl)thio]-3-methylphenyl}-2,2-dimethyl propanamide.

57. A compound corresponding to Formula IX:

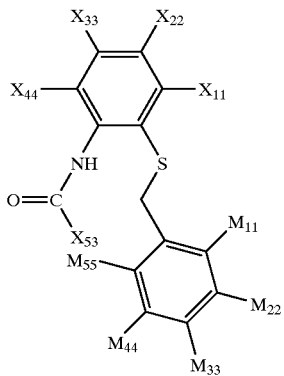

(IX)

wherein:

$M_{11}$, $M_{22}$, $M_{33}$, $M_{44}$, and $M_{55}$ are independently hydrogen, hydrocarbyl, substituted hydrocarbyl, hydroxy, hydrocarbyloxy, substituted hydrocarbyloxy, mercapto, halo, heterocyclo, nitro, amino, acylamino, acylthio, or acyloxy, provided an adjacent two of $M_{11}$, $M_{22}$, $M_{33}$, $M_{44}$, and $M_{55}$ form a fused ring with the atoms to which they are bonded;

$X_{11}$, $X_{22}$, $X_{33}$, and $X_{44}$, are independently hydrogen, hydrocarbyl, substituted hydrocarbyl, hydroxy, hydrocarbyloxy, substituted hydrocarbyloxy, mercapto, halo, heterocyclo, nitro, amino, acylamino, acylthio, acyloxy or acyl; and $X_{53}$ is hydrogen, hydrocarbyl, substituted hydrocarbyl, heterocyclo, or amino.

58. The compound of claim 57 wherein $X_{53}$ is heterocyclo, optionally substituted linear, branched or cycloalkyl, or optionally substituted phenyl.

59. The compound of claim 57 wherein one of $X_{11}$, $X_{22}$, $X_{33}$, $X_{44}$ is alkyl, nitro, or halo and the others of $X_{11}$, $X_{22}$, $X_{33}$, $X_{44}$ are hydrogen.

60. The compound of claim 57 wherein $M_{11}$ and $M_{22}$, $M_{22}$ and $M_{33}$, $M_{33}$ and $M_{44}$ or $M_{44}$ and $M_{55}$, and the atoms to which they are attached form a fused ring comprising —O—CH$_2$—O—CH$_2$— or —OCH$_2$O—, and the others of $M_{11}$, $M_{22}$, $M_{33}$, $M_{44}$ and $M_{55}$ are hydrogen, halogen, or nitro.

* * * * *